US010335382B2

(12) United States Patent
Hellmich et al.

(10) Patent No.: US 10,335,382 B2
(45) Date of Patent: Jul. 2, 2019

(54) USE OF HYDROGEN SULFIDE SYNTHESIS INHIBITORS FOR CANCER THERAPY

(71) Applicants: Mark Hellmich, Galveston, TX (US); Jia Zhou, League City, TX (US); Csaba Szabo, Seattle, WA (US)

(72) Inventors: Mark Hellmich, Galveston, TX (US); Jia Zhou, League City, TX (US); Csaba Szabo, Seattle, WA (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/967,649

(22) Filed: Dec. 14, 2015

(65) Prior Publication Data

US 2016/0095831 A1 Apr. 7, 2016

Related U.S. Application Data

(63) Continuation-in-part of application No. PCT/US2014/042440, filed on Jun. 14, 2014.

(60) Provisional application No. 61/834,984, filed on Jun. 14, 2013.

(51) Int. Cl.
| | |
|---|---|
| A61K 31/195 | (2006.01) |
| A61K 31/325 | (2006.01) |
| A61K 31/22 | (2006.01) |
| A61K 31/222 | (2006.01) |
| C12N 15/113 | (2010.01) |
| A61K 31/221 | (2006.01) |
| A61K 31/27 | (2006.01) |
| A61K 31/7105 | (2006.01) |
| A61K 45/06 | (2006.01) |
| C07C 291/04 | (2006.01) |

(52) U.S. Cl.
CPC ............ *A61K 31/195* (2013.01); *A61K 31/22* (2013.01); *A61K 31/221* (2013.01); *A61K 31/222* (2013.01); *A61K 31/27* (2013.01); *A61K 31/325* (2013.01); *A61K 31/7105* (2013.01); *A61K 45/06* (2013.01); *C07C 291/04* (2013.01); *C12N 15/1137* (2013.01); *C12Y 402/01022* (2013.01); *C12N 2310/14* (2013.01); *C12N 2310/531* (2013.01)

(58) Field of Classification Search
CPC .... A61K 31/195; A61K 31/221; A61K 31/27; A61K 31/7105; A61K 45/06; A61K 31/222; A61K 31/22; A61K 31/325; C07C 291/04; C12N 15/1137; C12Y 2310/531; C12N 2310/14; C12Y 402/01022
See application file for complete search history.

(56) References Cited

U.S. PATENT DOCUMENTS

| | | | |
|---|---|---|---|
| 2006/0241186 A1* | 10/2006 | Gerson | ................. A61K 31/13 514/589 |
| 2009/0233888 A1 | 9/2009 | Lin | .............................. 514/166 |
| 2012/0010230 A1 | 1/2012 | MacDougall et al. | ........ 514/278 |

FOREIGN PATENT DOCUMENTS

| | | | |
|---|---|---|---|
| FR | M1316 | * | 6/1962 |
| GB | 1446980 | | 8/1976 |

OTHER PUBLICATIONS

Asimakopoulou et al., "Selectivity of commonly used pharmacological inhibitors for cystathionine β synthase (CBS) and cystathionine γ lyase (CSE)", *Br J Pharmacol*, 169(4): 922-32, 2013.
Cai et al., "The novel proangiogenic effect of hydrogen sulfide is dependent on Akt phosphorylation", *Cardiovasc Res.*, 76: 29-40, 2007.
Cai et al., "Hydrogen sulfide induces human colon cancer cell proliferation: role of Akt, ERK and p21", *Cell Biol Int.*, 34: 565-72, 2010.
Cao et al., "Butyrate-stimulated H2S Production in Colon Cancer Cells" *Antioxidants & Redox Signaling* 12(9):1101-9, 2010.
Carmeliet and Jain, "Molecular mechanisms and clinical applications of angiogenesis", *Nature*, 473: 298-307, 2011.
Chao et al., "A function for the integrin alpha6beta4 in the invasive properties of colorectal carcinoma cells", *Cancer Res.*, 56: 4811-19, 1996.
Chen et al., "Production of the neuromodulator H2S by cystathionine beta-synthase via the condensation of cysteine and homocysteine", *J Biol Chem*, 279(50): 52082-86, 2004.
Coletta et al., "Hydrogen sulfide and nitric oxide are mutually dependent in the regulation of angiogenesis and endothelium-dependent vasorelaxation", *Proc Natl Acad Sci USA*, 109: 9161-66, 2012.
Cook and Figg, "Angiogenesis inhibitors: current strategies and future prospects", *CA Cancer J Clin.*, 60: 222-43, 2010.
Ettmayer et al., "Lessons learned from marketed and investigational prodrugs", *J Med Chem*, 47(10): 2393-2404, 2004.
Frank et al., "Purification and characterization of the wild type and truncated human cystathionine beta-synthase enzymes expressed in *E. coli*", *Arch Biochem Biophys*, 470: 64-72, 2008.
Frezza et al., "Organelle isolation: functional mitochondria from mouse liver, muscle and cultured fibroblasts", *Nat Protoc.*, 2: 287-95, 2007.

(Continued)

*Primary Examiner* — Sudhakar Katakam
(74) *Attorney, Agent, or Firm* — Norton Rose Fulbright US LLP

(57) ABSTRACT

In certain aspects the methods comprise administering an inhibitor of hydrogen sulfide biosynthesis, a cystathionine-β-synthase (CBS) inhibitor, or a hydrogen sulfide neutralizing agent to a patient having a cancer associated with elevated production of hydrogen sulfide.

1 Claim, 12 Drawing Sheets
Specification includes a Sequence Listing.

(56) References Cited

OTHER PUBLICATIONS

Goubern et al., "Sulfide, the first inorganic substrate for human cells", *FASEB J.*, 21: 1699-1706, 2007.

Hellmich et al., "The therapeutic potential of cystathionine β-synthetase/hydrogen sulfide inhibition in cancer", *Antiox Redox Sign*, 22(5): 424-48, 2014.

Huang et al., "Site-directed mutagenesis on human cystathionine-gamma-lyase reveals insights into the modulation of H2S production", *J Mol Biol*, 396: 708-18, 2009.

International Search and Written Opinion issued in PCT/US14/42440, dated Dec. 9, 2014.

International Preliminary Report on Patentability issued in PCT/US2014/042440, dated Dec. 23, 2015.

Kim et al., "Raf-1 kinase inhibitory protein (RKIP) mediates ethanol-induced sensitization of secretagogue signaling in pancreatic acinar cells", *J Biol Chem.*, 287: 33377-88, 2012.

Kimura, "Hydrogen sulfide: its production, release and functions", *Amino Acids*, 41: 113-21, 2011.

Li et al., "Hydrogen sulfide and cell signaling", *Ann Rev Pharmacol Toxicol.*, 51: 169-87, 2011.

Manna and Jain, "Hydrogen sulfide and L-cysteine increase phosphatidylinositol 3,4,5-trisphosphate (PIP3) and glucose utilization by inhibiting phosphatase and tensin homolog (PTEN) protein and activating phosphoinositide 3-kinase (PI3K)/serine/threonine protein kinase (AKT)/protein kinase Cζ/λ (PKCζ/λ) in 3T311 adipocytes", *J Biol Chem.*, 286: 39848-59, 2011.

Mathupala et al., "The pivotal roles of mitochondria in cancer: Warburg and beyond and encouraging prospects for effective therapies", *Biochim Biophys Acta.*, 1797:1225-30, 2010.

Modis et al., "Intramitochondrial hydrogen sulfide production by 3-mercaptopyruvate sulfurtransferase maintains mitochondrial electron flow and supports cellular bioenergetics", *FASEB J.*, 27: 601-11, 2013.

Mustafa et al., "Hydrogen sulfide as endothelium-derived hyperpolarizing factor sulfhydrates potassium channels", *Circ Res.*, 109: 1259-68, 2011.

Papapetropoulos et al., "Hydrogen sulfide is an endogenous stimulator of angiogenesis", *Proc Natl Acad Sci USA.*, 106: 21972-77, 2009.

Paul and Snyder, "H$_2$S signalling through protein sulfhydration and beyond", *Nat Rev Mol Cell Biol.*, 13: 499-507, 2012.

Rautio et al., "Prodrugs: design and clinical applications", *Nat Rev Drug Discov.*, 7: 255-70, 2008.

Schulze and Harris, "How cancer metabolism is tuned for proliferation and vulnerable to disruption", *Nature*, 491: 364-73, 2012.

Stipanuk and Beck, "Characterization of the enzymic capacity for cysteine desulphhydration in liver and kidney of the rat", *Biochem J*, 206: 267-77, 1982.

Suzuki et al., "Hydrogen sulfide replacement therapy protects the vascular endothelium in hyperglycemia by preserving mitochondrial function", *Proc Natl Acad Sci USA*, 108: 13829-34, 2011.

Szabo and Papapetropoulos, "Hydrogen sulphide and angiogenesis: mechanisms and applications", *Br J Pharmacol.*, 164: 853-65, 2011.

Szabo et al., "Tumor-derived hydrogen sulfide, produced by cystathionine-β-synthase, stimulates bioenergetics, cell proliferation, and angiogenesis in colon cancer", *Proc Natl Acad Sci USA*, 110: 12474-9, 2013.

Szabo, "Hydrogen sulphide and its therapeutic potential", *Nat Rev Drug Discov.*, 6: 917-935, 2007.

Szczesny et al., "Age-dependent deficiency in import of mitochondrial DNA glycosylases required for repair of oxidatively damaged bases", *Proc Natl Acad Sci USA.*, 100: 10670-75, 2003.

Tentler et al., "Patient-derived tumour xenografts as models for oncology drug development", *Nat Rev Clin Oncol.*, 9: 338-50, 2012.

Wu et al., "Multiparameter metabolic analysis reveals a close link between attenuated mitochondrial bioenergetic function and enhanced glycolysis dependency in human tumor cells", *Am J Physiol Cell Physiol.*, 292: C125-36, 2007.

Yang et al., "H2S as a physiologic vasorelaxant: hypertension in mice with deletion of cystathionine gamma-lyase", *Science*, 322: 587-90, 2008.

Zhang et al. "Hydrogen Sulfide Contributes to Hypoxia-induced Radioresistance on Hepatoma Cells" *J. Radiat. Res.* 52:622-28, 2011.

\* cited by examiner

USE OF HYDROGEN SULFIDE SYNTHESIS INHIBITORS FOR CANCER THERAPY

PRIORITY

This application is a continuation-in-part of and claims priority to International Application serial number PCT/US2014/042440, filed Jun. 14, 2014; and U.S. Provisional Patent Application Ser. No. 61/834,984 filed Jun. 14, 2013, each of which is incorporated herein by reference in its entirety.

STATEMENT REGARDING FEDERALLY FUNDED RESEARCH

This invention was made with government support under CA125209 awarded by the National Institutes of Health. The government has certain rights in the invention.

BACKGROUND

Colorectal cancer is a common form of cancer, the incidence of which is increasing worldwide. Various methods, including fecal occult blood test and colonoscopy, are currently used for screening colorectal cancer and have increased the rates of detection for early-stage cancer. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease, which may ultimately result in recurrence.

Thus, there remains a need for additional compositions and methods for treating cancer, particularly colorectal cancer.

SUMMARY

Certain embodiments are directed to methods for treating cancers associated with elevated production of hydrogen sulfide ($H_2S$), e.g., colorectal cancer. In certain aspects the methods comprise administering an inhibitor of hydrogen sulfide biosynthesis or a hydrogen sulfide neutralizing agent to a patient having a cancer associated with elevated production of hydrogen sulfide. In certain aspects, the biosynthesis of $H_2S$ can be inhibited by administering a cystathionine-β-synthase (CBS) inhibitor. In certain aspects the inhibitor is administered as a prodrug. In further aspects the patient has colorectal cancer. As used herein, a cancer associated with elevated production of hydrogen sulfide is a cancer cell that has a level of $H_2S$ that is higher than non-cancerous cells of similar origin. The patient can be a human or an animal (i.e., the methods can be applied in a medical, laboratory, or veterinary setting).

In certain aspects a patient is administered an inhibitor of hydrogen sulfide biosynthesis. $H_2S$ can be synthesized by the desulfuration of cystine/cysteine by three enzymes; cystathionine beta synthase (CBS; EC 4.2.1.22), cystathionine gamma lyase (CSE; EC 4.4.1.1) and mercaptopyruvate sulfurtransferase (MST; EC 2.8.1.2). MST is found both in the mitochondria and cytosol while CBS and CSE are mainly in the cytosol. $H_2S$ biosynthesis can be reduced or inhibited by inhibiting CBS. In other aspects, products or allosteric regulators of CBS can be administered or induced in order to regulate the biosynthesis of $H_2S$. In certain aspects a CBS inhibitor includes, but is not limited to interfering RNA (RNAi)(e.g., shRNA), D,L-propargylglycine (PAG), beta cyanoalanine (BCA), L-aminoethoxyvinylglycine (AVG), aminooxyacetic acid (AOAA), trifluoroalanine, hydroxylamine (HA), d-cycloserine and isoniacid. In certain aspects a CBS inhibitor can be selected from Table 1.

TABLE 1

| CBS inhibitors | |
|---|---|
| Compound | Inhibition of CBS activity at 100 μM |
| AOAA | 98% |
| 2,3-Dimethoxy-1,4-naphthoquinone | 98% |
| Demeclocycline hydrochloride | 96% |
| Rottlerin | 96% |
| Y-27632 | 94% |
| GW5074 | 87% |
| 6-Hydroxy-DL-DOPA | 77% |
| Me-3,4-dephostatin | 85% |
| Zafirlukast | 81% |
| Aurintricarboxylic acid | 75% |
| GW7647 | 73% |
| Closantel | 72% |
| Acriflavinium | 64% |
| Eseroline fumarate | 60% |
| Raloxifene | 60% |
| Bexarotene | 58% |
| Suramin sodium | 57% |
| Doxycycline | 57% |
| Estradiol | 53% |
| Phenserine | 53% |
| Doxorubicin | 52% |
| Shikonin | 51% |
| Hexestrol | 50% |
| Carbidopa | 45% |
| Retinoic acid | 43% |
| Tetracycline | 43% |
| Lithocholic acid | 42% |
| Propidium iodide | 41% |
| Calcifediol | 32% |
| Mephenytoin | 32% |
| A-77636 hydrochloride | 30% |
| Ibudilast | 30% |
| Troglitazone | 30% |

Certain embodiments are directed to prodrug compositions and methods comprising administration of a prodrug. In certain aspects the prodrug includes, but is not limited to a benzyl ester, methyl ester, or carbamate of a CBS inhibitor listed in table 1. In a further aspect the prodrug is an AOAA ester, such as an AOAA alkyl ester.

In certain aspects a hydrogen sulfide neutralizing agent can be administered to a patient or cancer cell. $H_2S$ neutralizing agents include diethylmaleate (DEM) and/or a glyoxal. Glyoxal is an organic compound with the formula OCHCHO, and includes hydrates or polymers thereof.

In certain aspects the inhibitor of hydrogen sulfide biosynthesis, the cystathionine-β-synthase (CBS) inhibitor, or the hydrogen sulfide neutralizing agent is administered directly to a cancer cell, e.g., by intra-tumoral injection.

In certain aspects the colorectal cancer has a Kras mutation.

The methods can further comprise testing or assessing a cancer for $H_2S$ production before, during, and/or after administration of a therapy. In certain aspects, the expression level or enzymatic activity of CBS is determined before, during, and/or after administration of a therapy. In certain aspects, expression or activity is elevated if the protein or encoding nucleic acid is present, or enzymatic activity is more than 1.5, 2, 2.5, or 3 times higher than a reference or adjacent non-cancer tissue or cell. In such cases, the cancer can be characterized as overexpressing CBS.

Certain embodiments are directed to a compound having a chemical structure of Formula I:

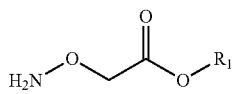

Formula I wherein $R_1$ is a ethyl, n-propyl, iso-propyl, n-butyl, sec-butyl, iso-butyl, tert-butyl, n-pentyl, tert-pentyl, neo-pentyl, iso-pentyl, sec-pentyl, or 3-pentyl group. In certain aspects $R_1$ is a 3-pentyl group. The method can comprise administering a compound of Formula I to a patient having a cancer associated with elevated production of hydrogen sulfide. In certain aspects the cancer is colorectal cancer. The compound can be administered by intra-tumoral injection. In certain aspects the cancer has a Kras mutation. The method can further comprise measuring $H_2S$ levels in a cancer sample from the patient before administering the compound. The method can further comprise administering a second anti-cancer agent. In certain embodiments the compound is YD-2-51.

As used herein, an "inhibitor" can be any chemical compound or small molecule that can reduce the activity or function of a protein, such as CBS. An inhibitor as provided by the invention, for example, can inhibit directly or indirectly the activity of a protein. Direct inhibition can be accomplished, for example, by binding to a protein and thereby preventing the protein from binding an intended target, such as a receptor, or by inhibiting an enzymatic or other activity of the protein, either competitively, non-competitively, or uncompetitively. Indirect inhibition can be accomplished, for example, by binding to a protein's intended target, such as a substrate, receptor, or binding partner, thereby blocking or reducing activity of the protein.

"Prodrug" refers to a derivative of an active CBS inhibitor (drug) that may require a transformation under the conditions of use, such as within the body, to release the active CBS inhibitor. Prodrugs are frequently, but not necessarily, pharmacologically inactive until converted into the active drug. Prodrugs are typically obtained by masking one or more functional groups in an active drug believed to be in part required for activity with a progroup to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A "therapeutically effective amount" in reference to the treatment of cancer, means an amount capable of invoking one or more of the following effects: (1) inhibition, to some extent, of cancer or tumor growth, including slowing growth or complete growth arrest; (2) reducing the number of cancer cells; (3) reduction in tumor size; (4) inhibition (i.e., reduction, slowing down, or complete stopping) of cancer cell infiltration into peripheral organs; (5) inhibition (i.e., reduction, slowing down, or complete stopping) of metastasis; (6) enhancement of anti-tumor immune response, which may, but is not required to, result in the regression or rejection of a tumor comprising cancer cells, or (7) relief, to some extent, of one or more symptoms associated with the cancer. The therapeutically effective amount may vary according to factors such as the disease state, age, sex and weight of the individual and the ability of one or more anti-cancer agents to elicit a desired response in the individual. A "therapeutically effective amount" is also one in which any toxic or detrimental effects are outweighed by the therapeutically beneficial effects.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

The term "Kras mutation" includes any one or more mutations in the Kras (which can also be referred to as KRAS2 or RASK2) gene. Examples of Kras mutations include, but are not limited to, G12S, G12D, G12A, G12V, G12R, G12C, G13D, and combinations thereof.

Other embodiments of the invention are discussed throughout this application. Any embodiment discussed with respect to one aspect of the invention applies to other aspects of the invention as well and vice versa. Each embodiment described herein is understood to be applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
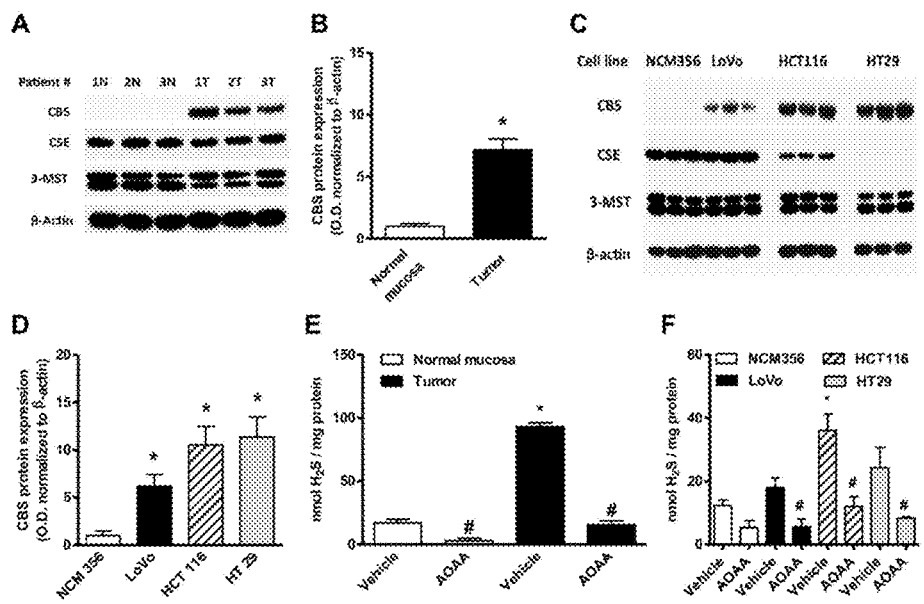
FIG. 1. CBS is overexpressed in human colorectal cancer. (A) Representative Western blot of CBS, CSE and 3-MST protein expression in human colorectal cancer specimens, paired with the corresponding normal mucosa tissues. PVDF membranes were probed with rabbit polyclonal antibodies against CBS, CSE and 3-MST. (B) Densitometric analyses of CBS expression, in seven pairs of human colorectal cancers and the patient-matched normal mucosa, showed an approximately seven-fold increase in CBS protein expression in colon cancer (arbitrary relative densitometric units were normalized with β-actin using image analysis software) ($*p<0.05$ vs. normal mucosa). (C, D) CBS was highly expressed in three different colon cancer cell lines (LoVo, HCT116 and HT29); low expression was detected in the non-tumorigenic normal colon mucosa cells (NCM356) (arbitrary relative densitometric units were normalized with β-actin using image analysis software) ($*p<0.05$ vs NCM356 cells) (E) or in colon cancer cell lines (F) by the methylene blue method. $H_2S$ production was stimulated in tissue or cell lysates by incubation at 37° C. (30 min) in presence of the CBS substrates L-cysteine (3 mM) and L-homocysteine (0.5 mM). CBS activity was significantly higher in colon cancer tissues, when compared to their corresponding controls. AOAA (1 mM) blocked the $H_2S$-producing activity of CBS in the tissue extracts ($*p<0.05$ vs. corresponding from normal mucosa and # $p<0.05$ vs. vehicle). (F) HCT116 cells exhibited the highest rate of $H_2S$ production, as measured by methylene blue method in cell lysates ($*p<0.05$ vs. corresponding values in NCM356 and # $p<0.05$ vs. vehicle). Western blots show representatives of at least n=3 experiments; $H_2S$ measurements represent mean±SEM of at least n=3 determinations.

The physiological functions of the endogenous gasotransmitter hydrogen sulfide ($H_2S$) include vasorelaxation, stimulation of cellular bioenergetics, and promotion of angiogenesis. Analysis of human colon cancer biopsies and patient-matched normal margin mucosa revealed the selective upregulation of the $H_2S$-producing enzyme cystathionine-β-synthase (CBS) in colon cancer. Similarly, colon cancer-derived epithelial cell lines (HCT116, HT-29, LoVo) exhibited selective CBS upregulation, when compared to the nonmalignant colonic mucosa cells (NCM356). Colon cancer cells exhibited an increased rate of $H_2S$ production, which was further stimulated by intracellular calcium mobilizing agents. CBS exhibited mitochondrial as well as cytosolic localization. Lentiviral silencing of CBS or its pharmacological inhibition with amino-oxyacetic acid (AOAA) reduced the proliferation, migration, and invasion of colorectal cancer cells; reduced endothelial cell migration in co-cultures; and suppressed mitochondrial functions (including oxygen consumption, ATP turnover and respiratory reserve capacity) as well as glycolysis (including GAPDH activity). Treatment of nude mice with AOAA attenuated the growth of patient-derived colon cancer xenografts and reduced tumor blood flow. Similarly, CBS silencing of the tumor cells decreased xenograft growth and neovessel density. In contrast to CBS, silencing of cystathionine-γ-lyase (CSE, another $H_2S$-producing enzyme, the expression of which was unaltered in colon cancer) did not affect tumor cell growth or bioenergetics. Colon cancer cells selectively overexpressing CBS, produce $H_2S$ to (a) maintain cellular bioenergetics, thereby supporting tumor growth, and (b) promote angiogenesis and vasorelaxation, which helps to provide the tumor with blood and nutrients. The inventors identify CBS as a tumor survival factor and anticancer drug target.

I. HYDROGEN SULFIDE ($H_2S$)

Hydrogen sulfide is the chemical compound with the formula $H_2S$. It is a colorless gas having a foul odor. $H_2S$ is heavier than air, very poisonous, corrosive, flammable, and explosive. Hydrogen sulfide often results from the bacterial breakdown of organic matter in the absence of oxygen, such as in swamps and sewers; this process is commonly known as anaerobic digestion. $H_2S$ also occurs in volcanic gases, natural gas, and some well waters. The human body produces small amounts of $H_2S$ and uses it as a signaling molecule.

Hydrogen sulfide is produced in small amounts by some cells of the mammalian body and has a number of biological signaling functions (only two other such gases are currently known: nitric oxide (NO) and carbon monoxide (CO)). $H_2S$ is generated from L-cysteine by two pyridoxal-5'-phospate-dependent enzymes, cystathionine-β-synthase (CBS) and cystathionine-γ-lyase (CSE) and by the combined action of cysteine aminotransferase and 3-mercaptopyruvate sulfurtransferase (3-MST) (Szabo (2007) *Nat Rev Drug Discov.* 6:917-935; Kimura (2011) *Amino Acids* 41:113-21; Li et al. (2011) *Ann Rev Pharmacol Toxicol.* 51:169-87). Hydrogen sulfide ($H_2S$) is a stimulator of vasorelaxation (Yang et al. (2008) *Science* 322:587-90; Mustafa et al. (2011) *Circ Res.* 109:1259-68; Coletta et al. (2012) *Proc Nall Acad Sci USA.* 109:9161-66), angiogenesis (Coletta et al. (2012) *Proc Natl Acad Sci USA.* 109:9161-66; Cai et al. (2007) *Cardiovasc Res.* 76:29-40; Papapetropoulos et al. (2009) *Proc Natl Acad Sci USA.* 106:21972-77) and cellular bioenergetics (Goubern et al. (2007) *FASEB J* 21:1699-1706; Módis et al. (2013) *FASEB J* 27:601-11). $H_2S$ exerts its cellular actions via multiple mechanisms including activation of potassium channels (Yang et al. (2008) *Science* 322:587-90; Mustafa et al. (2011) *Circ Res.* 109:1259-68; Coletta et al. (2012) *Proc*

Natl Acad Sci USA. 109:9161-66), stimulation of kinase pathways (Cai et al. (2007) Cardiovasc Res. 76:29-40: Cai et al. (2010) Cell Biol Int. 34:565-72; Manna and Jain (2011) J Biol Chem. 286:39848-59) and inhibition of phosphodiesterases (Coletta et al. (2012) Proc Natl Acad Sci USA. 109:9161-66; Paul and Snyder (2012) Nat Rev Mol Cell Biol. 13:499-507). Eventually the gas is converted to sulfite in the mitochondria by thiosulfate reductase, and the sulfite is further oxidized to thiosulfate and sulfate by sulfite oxidase. The sulfates are excreted in the urine.

Both ATP generation and angiogenesis are vital factors for the growth and proliferation of tumors (Mathupala et al. (2010) Biochim Biophys Acta. 1797:1225-30; Schulze and Harris (2012) Nature 491:364-73; Carmeliet and Jain (2011) Nature 473:298-307; Cook and Figg (2010) CA Cancer J Clin. 60:222-43). Using human colon cancer tissues and cancer-derived cell lines, the inventors have conducted a series of in vitro and in vivo studies to explore whether endogenous, tumor cell-derived $H_2S$ plays a role as a tumor-derived survival factor. The results show that CBS is selectively overexpressed in colon cancer, and that $H_2S$ produced by it serves to maintain the tumor's cellular bioenergetics and to promote tumor angiogenesis.

As a result of the CBS overexpression, $H_2S$ is overproduced in colon cancer cells. $H_2S$ serves as an inorganic electron donor, stimulating mitochondrial electron transport, increasing ATP turnover. In addition, it increases the glycolytic activity of the tumor cell. Via these autocrine bioenergetic effects, $H_2S$ stimulates cancer cell proliferation, migration and invasion. In addition, $H_2S$ diffuses into the surrounding cells and tissues, stimulating angiogenesis, as well as acting as a vascular relaxant. Via these paracrine effects, $H_2S$ promotes the supply of blood and nutrients to the tumor.

$H_2S$ production can be measured in a tissue homogenate by using a methylene blue assay. Briefly, 1% zinc acetate is added to a tissue homogenate to trap $H_2S$ followed by 10% trichloroacetic acid to precipitate proteins. Subsequently, N,N-dimethyl-phenylenediamine sulfate in 7.2 M HCl immediately followed by addition of $FeCl_3$ in 1.2 M HCl. The absorbance of the resulting solution is measured at 655 nm. $H_2S$ content is calculated against a calibration curve of standard $H_2S$ solutions.

II. CYSTATHIONINE-β-SYNTHASE (CBS) INHIBITORS AND PRODRUGS

CBS-derived hydrogen sulfide ($H_2S$) is a tumor growth factor and thus a promising chemotherapy target. In colorectal cancer, selective upregulation of CBS induces production of $H_2S$ with resulting stimulation of tumor cell bioenergetics, growth, proliferation, migration and invasion (Szabo et al., PNAS, 2013; Hellmich et al., Antiox Redox Sign, 2014). Currently, the most potent inhibitor of CBS known is aminooxyacetic acid (AOAA), which exerts potent anticancer effects in vitro and in vivo (Szabo et al., PNAS, 2013). Other CBS inhibitors are identified in table 1. In certain aspects the CBS can be coupled to a progroup to form a prodrug of the respective compounds.

Prodrugs are derivatives of drug compounds that require transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

Prodrug compounds useful in the methods described herein are generally compounds that when administered in an amount effective to, and under conditions suitable to, yield an amount of a drug compound effective to inhibit CBS and proliferation of cancer cells.

A progroup can include, but is not limited to, a group or moiety that is metabolized under the conditions of use to yield a CBS inhibitor. In some embodiments, the progroup may be, but is not limited to, an acid labile hydroxyalkyl-containing progroup, an acid labile thio containing progroup, an acid labile amino containing progroup, an acid labile phosphate containing progroup, and salts thereof. Each of the acid labile thio containing progroup and the acid labile amino containing progroup may be thioalkyl and aminoalkyl groups, respectively. In some embodiments the acid labile hydroxyalkyl-containing progroup, acid labile thio containing progroup, and an acid labile amino containing progroup may be capped as the corresponding phosphate, e.g., $—CH_2—O—P(O)(OH)_2$, thiophosphate, e.g. $—CH_2—S—P(O)(OH)_2$, and phosphoramidate, e.g. $—CH_2—NH—P(O)(OH)_2$, respectively, to make prodrug groups. These prodrug groups can be free acids as depicted, alkyl esters, or salts, e.g. metal salts, and combinations thereof.

The mechanism by which the progroup is cleaved or metabolized is not critical, and can be caused by, for example, hydrolysis under the acidic conditions of the stomach, and/or by enzymes present in the digestive tract and/or tissues or organs of the body. Indeed, the progroup(s) can be selected to metabolize at a particular site within the body. For example, many esters are cleaved under the acidic conditions found in the stomach. Alternatively, the progroups may be designed to cleave or metabolize in the presence of enzymes such as esterases, amidases, lipolases, phosphatases including ATPases and kinase etc. Progroups including linkages capable of metabolizing in vivo to yield an active compound are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

The identity of the progroup can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, *J. Med. Chem.* 47(10:2393-2404).

The cell-based potency of a CBS inhibitor can be improved by synthesis of cell-permeable prodrugs of a CBS inhibitor. For instance, YD-1-71 (aminooxyacetic acid methyl ester) markedly enhances the antiproliferative effect of its parent, AOAA, in HCT116 human colonic epithelial cancer cells. Development of prodrugs of CBS inhibitors (e.g., AOAA) will enhance physicochemical, biopharmaceutical and pharmacokinetic properties of the inhibitors to improve cell permeability, efficacy and oral bioavailability, while reducing side effects in comparison with the parent drug.

Rational Design and Synthesis of Diverse Prodrug Forms of AOAA.

Developing prodrugs of AOAA will make it more lipophilic by making various esters or amides or other prodrug forms, which can be hydrolyzed by enzymes to release the parent drug in cancer cells. For example, YD-1-71 (AOAA methyl ester) markedly enhances the antiproliferative effect of its progenitor, AOAA. The prodrugs possess enhanced physicochemical, biopharmaceutical and pharmacokinetic properties such as better cell permeability, better oral bioavailability, improved pharmacokinetic profile and lower side effects in comparison with the parent drug.

Figure 8:
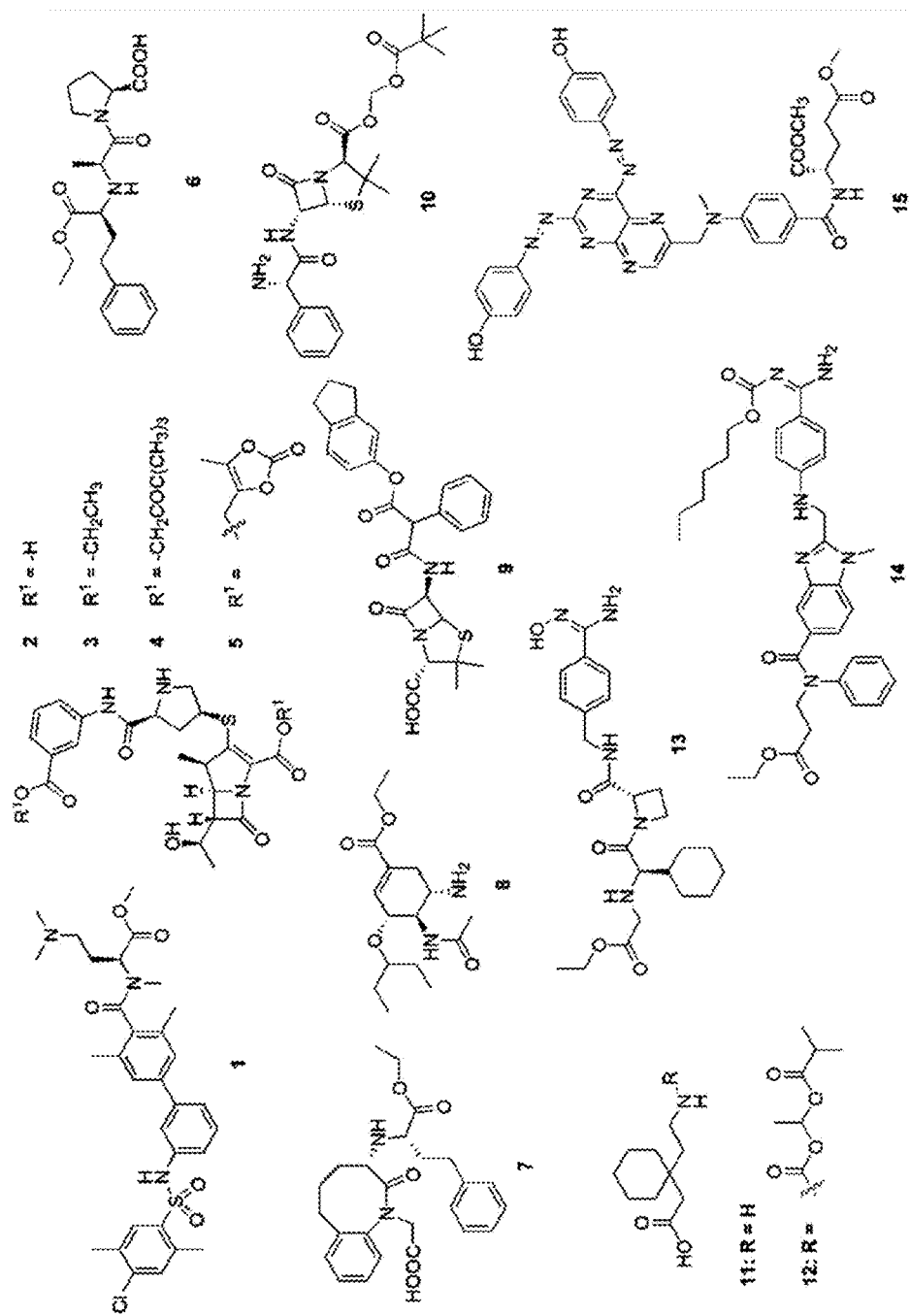
FIG. 8. Illustrates various chemical structures of examples of successful prodrugs.

AOAA is the most potent CBS inhibitor identified to date. However, AOAA has limited drug-like properties such as small molecular size, high polarity (low cLogP value of −0.79), and limited cell permeability. To advance the clinical translation of AOAA a prodrug strategy is used based on the success of numerous commercial prodrugs (FIG. 8).

Generally, ester prodrugs are most commonly used to enhance the lipophilicity and membrane permeability of water-soluble drugs by masking charged groups such as carboxylic acids. Novartis Inc. has reported the methyl ester prodrug (1) for enhanced oral exposure of the parent compound. Merck Inc. has developed several ester prodrugs of Ertapenem (2) to reduce the polarity and improve oral absorption. Ester prodrugs (3-5) demonstrated a significantly improved in vivo pharmacokinetic profile including oral bioavailability and could be rapidly hydrolyzed in the plasma to release Ertapenem. Other FDA-approved ethyl ester prodrugs, including Enalapril (6), Benazepril (7) and Oseltamivir (8), also have improved oral bioavailability, compared to corresponding parent drugs. In addition, more chemically diversified alkyl and aryl ester prodrugs such as 9, 10 are successfully used in preclinical and clinical development.

Amide prodrugs are relatively less commonly used than ester prodrugs, because of the higher relative stability of amides toward metabolic hydrolysis. However, this higher stability may increase the half-life of the prodrugs in vivo, followed by eventual hydrolysis and bioconversion into the active principle. Gabapentin (11) is an analog of the inhibitory neurotransmitter gamma-aminobutyric acid (GABA). Its amide prodrug (Gabapentin enacarbil, 12) provides improved bioavailability and is a successful marketed drug. Oximes, which could be hydrolyzed to ketones or amidines by the versatile microsomal cytochrome P450 (CYP450) enzymes, are used to enhance the membrane permeability and absorption. Ximelagatran (13) and Dabigatran (14) represent examples of ester/oxime prodrugs with improving oral bioavailability compared to the parent compound. The colon-specific azo based prodrugs of marketed anticancer agents such as methotrexate have also been reported recently: the prodrug (15) is metabolized by intestinal azoreductase enzymes to release the parent drug in the colon.

Figure 9:
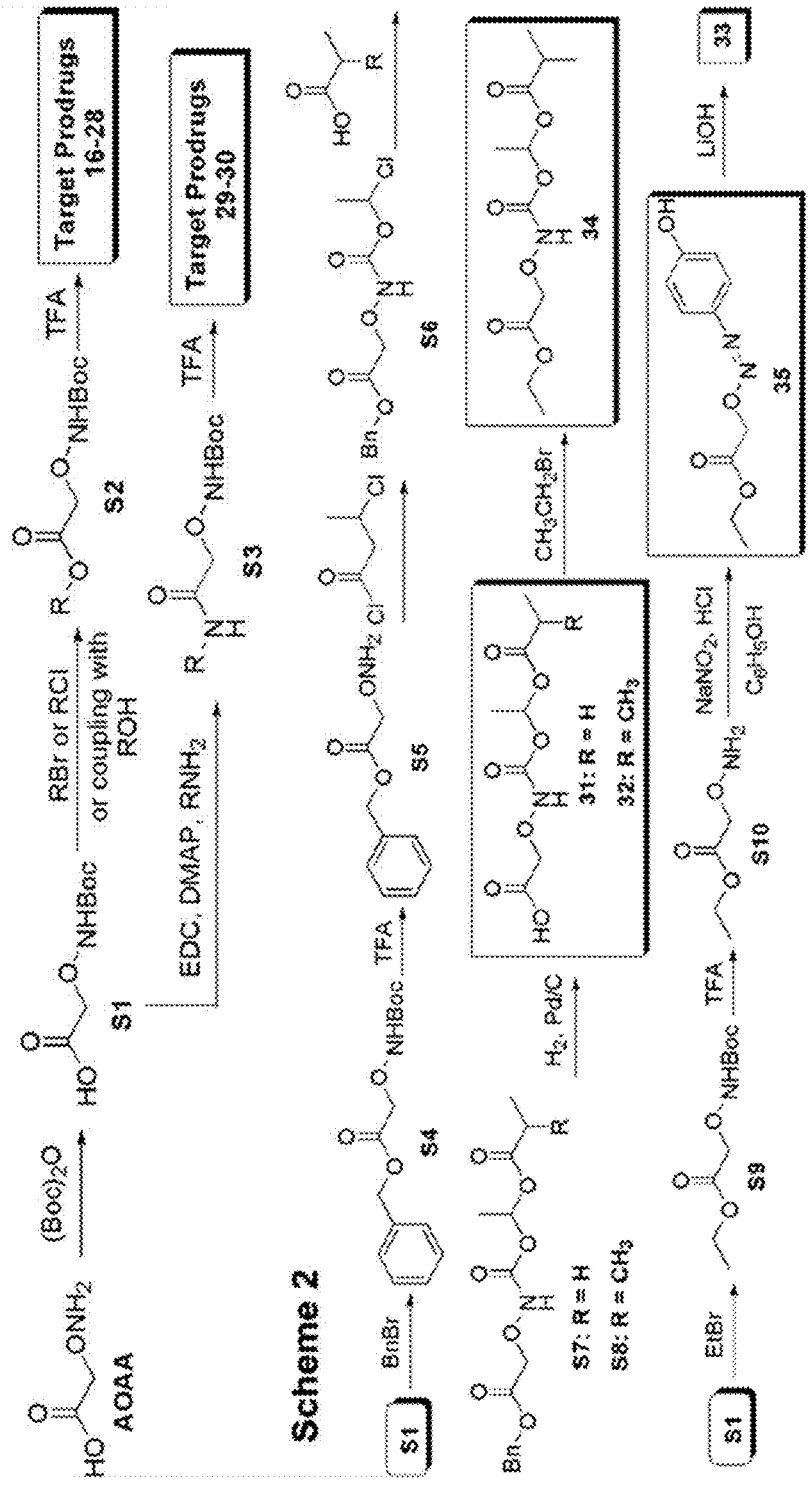
FIG. 9. Illustrates synthetic routes for prodrugs.
Figure 10:
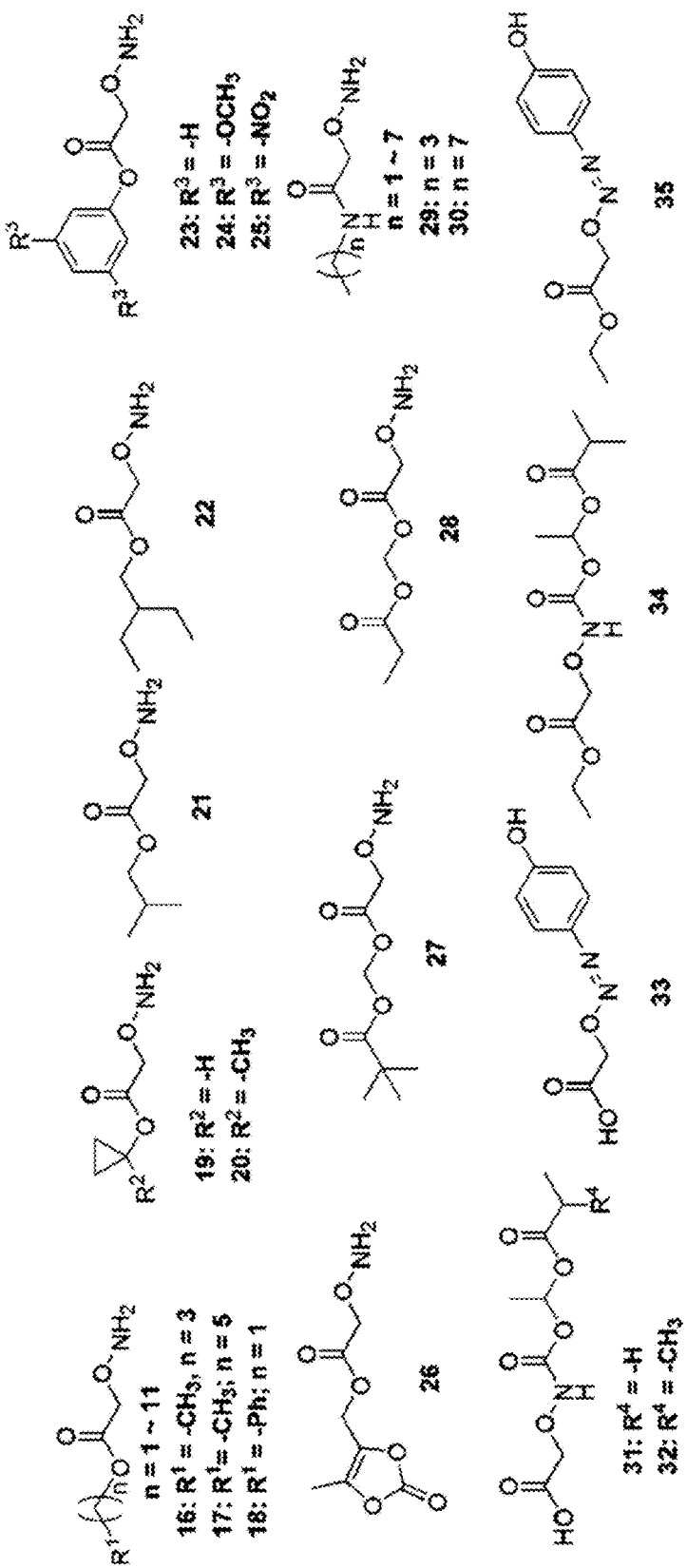
FIG. 10. Illustrates examples of chemical structures of the AOAA prodrugs.
Figure 11:
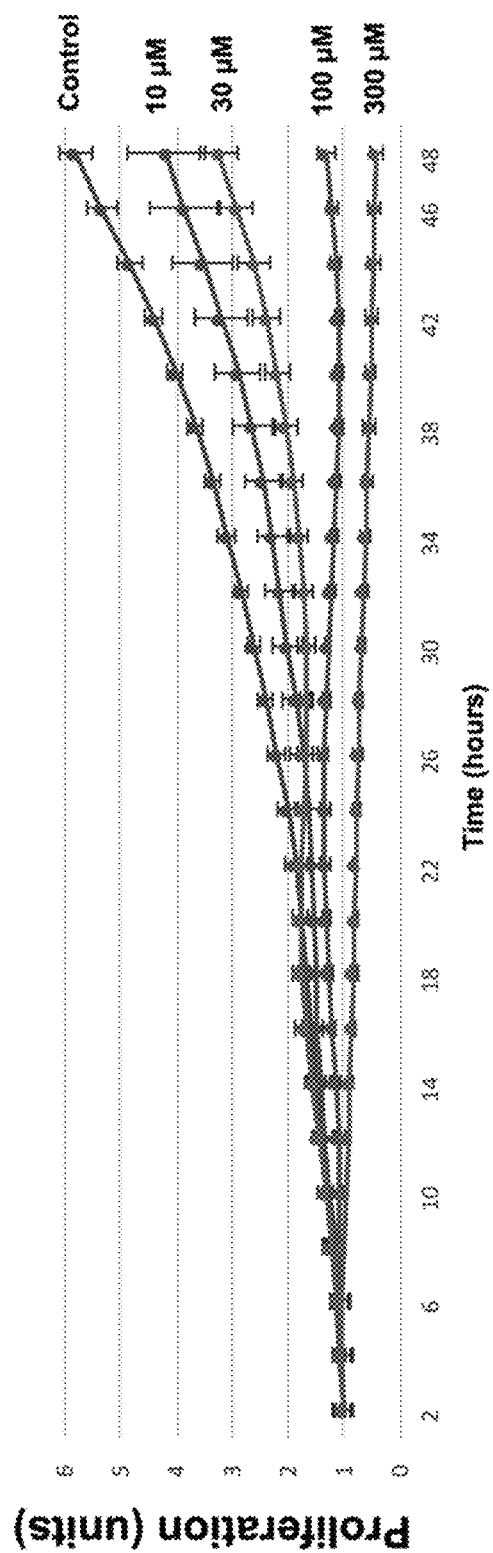
FIG. 11. Illustrates inhibition of colon cancer cell proliferation by YD-2-51.
Figure 12:
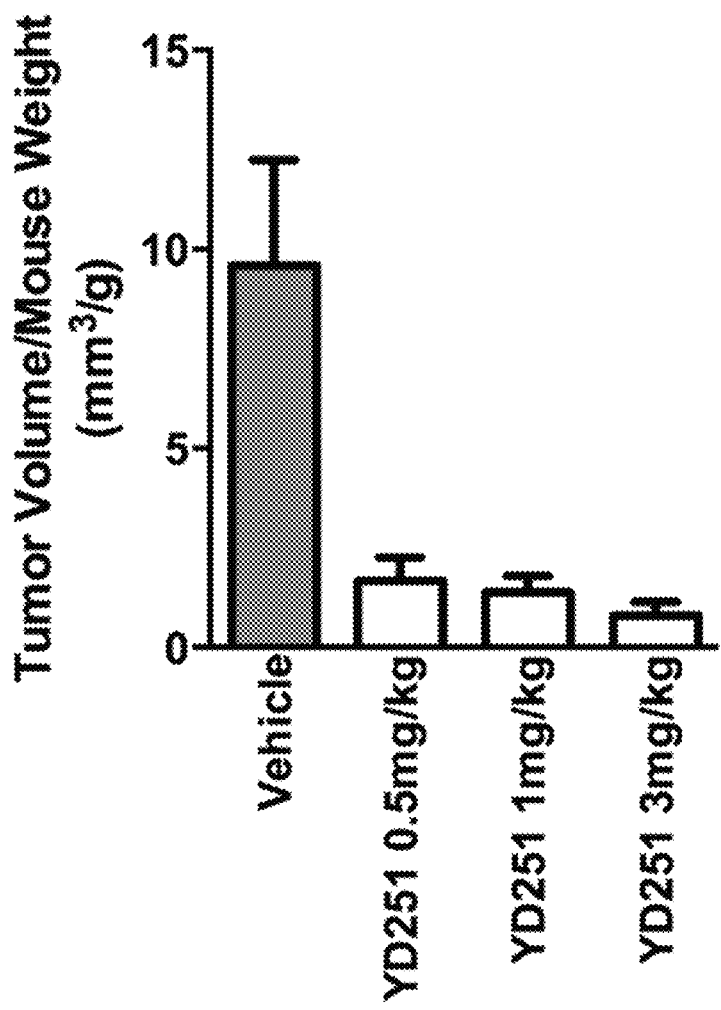
FIG. 12. Illustrates inhibition of tumor growth by YD-2-51 in tumor-bearing mice.

Developing appropriate prodrug forms of AOAA as a CBS inhibitor provides a viable approach for novel colorectal cancer therapy. As depicted in FIG. 9 and FIG. 10, a number of representative ester, amide or azo prodrugs have been designed by introduction of an appropriate lipophilic carrier from the acid or amino groups. These newly designed prodrugs have significantly improved C log P values in comparison with AOAA, which has a C log P value of −0.79. For example, the C log P values of prodrugs 18, 24, 30, 33 and 35 are 2.58, 1.24, 1.54, 2.27, and 2.71, respectively, and therefore have improved cell permeability according to Lipinski's "Rule of Five".

The synthetic methods for representative ester, amide or azo prodrugs are outlined in FIG. 9. The amino group of AOAA is protected with Boc to give the key intermediate S1. The substitution reaction between acid of S1 and various brominated/chlorinated reagents generates different esters S2. The target prodrugs 16-28 are obtained by Boc-deprotection with trifluoroacetic acid (TFA). The condensation reaction between S1 and various amines in the presence of EDC and DMAP produce corresponding amides S3. Target compounds 29 and 30 are synthesized by Boc-deprotection using TFA. As shown in Scheme 2, reaction of the key intermediate S1 with benzyl bromide in the presence of $K_2CO_3$ gives S4, and the subsequent Boc-deprotection yields benzyl AOAA S5.

Carbamate ester S6 is synthesized by the reaction of S5 with acid chloride. Ester intermediates S7 and S8 are prepared from S6 using different acids in the presence of $K_2CO_3$. The reduction of S7 and S8 affords target prodrugs 31 and 32. The prodrug 34 is obtained by coupling of 32 with bromoethane.

Ester S9 is synthesized from S1, followed by Boc-deprotection to yield ethyl AOAA S10. The intermediate S10 is treated with $NaNO_2$ and phenol in the presence of hydrochloric acid to achieve desired prodrug 35. The subsequent hydrolysis of 35 provides the prodrug 33.

Evaluating Prodrugs of AOAA Both in a Cell-Free CBS Enzyme Activity Assay, and a Cell Proliferation Assay Using HCT116 Colon Cancer Cells.

Studies have been performed characterizing, in detail, the specificity and selectivity of all known $H_2S$ biosynthesis inhibitors, using recombinant CBS and CSE enzymes. These studies used full-length human CBS enzyme, and a colorimetric 'capture' reaction of the $H_2S$ produced by these enzymes, an assay generally known as the 'methylene blue assay'. This assay is used in a 96-well plate format, as well as in combination with a second screening method based on a fluorescent dye.

In the first set of the experiments, the potency of the prodrugs synthesized is tested in a recombinant enzyme assay. These compounds are 'activated' and the CBS inhibitory effect will be restored, when the compounds are incubated with the cytosolic homogenates of HCT116 cells—subjecting the prodrugs to enzymatic bioactivation by cytosolic esterases. The prodrugs are converted to AOAA by HCT116 extracts, but do not undergo degradation in PBS and are only minimally be metabolized by plasma esterases. The prodrugs that demonstrate preferential conversion to AOAA in the HCT116 cell extracts as compared to the non-tumorigenic epithelial cell NCM356 cell extracts are identified as higher priority for further medicinal chemistry optimization.

There are several reports showing the existence of cancer-cell-specific or semi-specific esterases (e.g. N-acylaminoacylpeptide hydrolase, polyisoprenylated methylated protein methyl esterase and carboxylesterase 2); thus, some of the ester prodrugs of AOAA exhibit preferential conversion to AOAA by tumor cells. Cancer-cell-selective conversion of AOAA is not an absolute requirement, as cancer-cell preference of AOAA-mediated CBS inhibition is already ensured by findings that cancer cells express higher levels of CBS than normal/non-transformed cells. Nevertheless, cancer cell-selectivity is noted and compounds exhibiting selectivity or semi-selectivity receive higher priority for testing and further optimization.

Cellular proliferation assays are conducted in HCT116 CRC cells in vitro, using the Roche XCelligence method. Concentration-response curves with the various AOAA analogs are prepared (concentration range: 1, 3, 10, 100, 300 and 600 μM). AOAA is used as the reference control, which, according to preliminary data, has an $IC_{50}$ of approximately 300 μM. Control proliferation studies in the non-carcinogenic colonic epithelial cell line NCM356 are used to confirm cancer-cell selectivity. Since the NCM356 cells contain low levels of CBS, based on previous studies it is expect that AOAA (and its prodrugs) will only exert modest antiproliferative effects in these cells. Proliferation-inhibitory effects of the AOAA prodrugs in NCM356 cells indicate CBS-independent pharmacological actions. A collection of human colorectal tumor tissue samples (and surrounding non-cancerous tissue) are used to test the conversion of the AOAA prodrugs to AOAA in a number of cancer samples.

After the synthesis and testing of the compounds are subjected to a second medicinal chemistry optimization cycle, followed by the in vitro testing.

Evaluating AOAA Prodrugs in a Preclinical Model of Colon Cancer.

Figure 5:
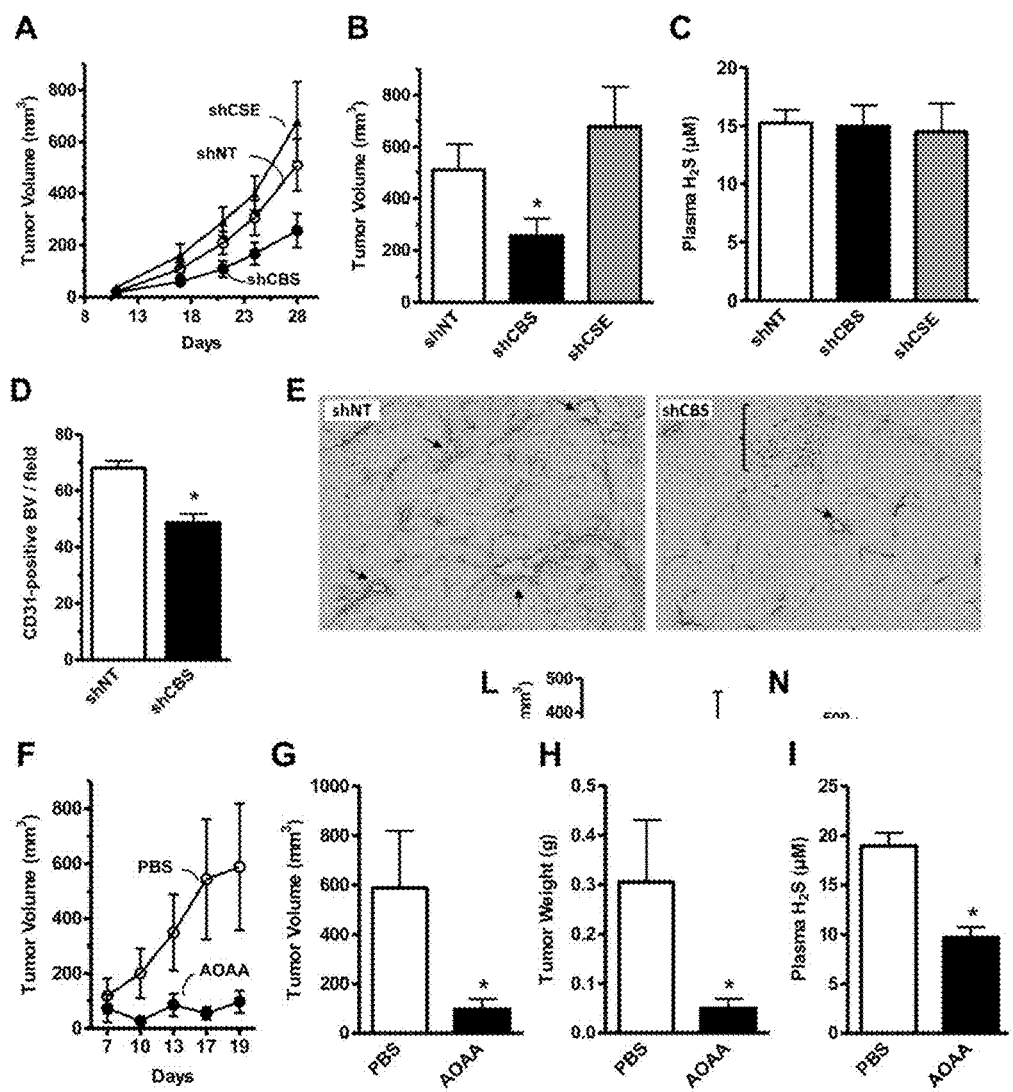
FIG. 5. ShRNA mediated down-regulation of CBS or pharmacological inhibition by AOAA inhibits colon cancer growth and tumor angiogenesis in vivo. Effects of shRNA-mediated gene silencing of CBS (shCBS) and CSE (shCSE) on HCT116 tumor xenograft: (A) growth rate (shNT=non-targeting shRNA control), (B) tumor volume at harvest (*p=0.04), and (C) plasma levels of $H_2S$. (D) Quantification of the effects of CBS silencing on CD31-positive blood vessel (BV) density in HCT116 tumor xenografts (*p<0.0001). (E) Photomicrographs of representative sections (10 μm) from control (shNT) and CBS knockdown (shCBS) xenografts showing CD31-positive BV. Note the increased density of BV in shNT vs. shCBS. Arrows indicate larger vessels and bracket indicates areas of necrosis with shCBS xenograft. Effects of AOAA or vehicle (PBS) on HCT116 tumor xenografts: (F) growth rate, (G) tumor volume (*p=0.02), (H) wet weight (*p=0.001), and I) plasma concentrations of $H_2S$ (*p=0.0005). (J) Photomicrographs of H&E stained formalin-fixed paraffin-embedded sections (5 μm) of the primary colon adenocarcinoma from a patient with stage III disease and Kras mutation (PT), and the corresponding patient-derived tumor xenograft (PDTX). Note the similar morphology of both specimens. (K) Western blot comparing the relative levels of expression of CBS in tissue extracts from the patient's tumor (T) shown in panel J and adjacent normal (N) mucosa. (L, M) Effects of AOAA and PBS treatment of growth rates of PDTXs from patient 1 and patient 2, respectively. (N) Summary data from two independent experiments showing the effects of AOAA and PBS on the change in PDTX volume over a seven-day course of treatment (*p=0.07). Photomicrographs of histological sections are representative of at least n=6 sections; tumor volume/weight data and $H_2S$ measurements represent mean±SEM of tumors/plasma values obtained from n=6 mice.
Figure 5:
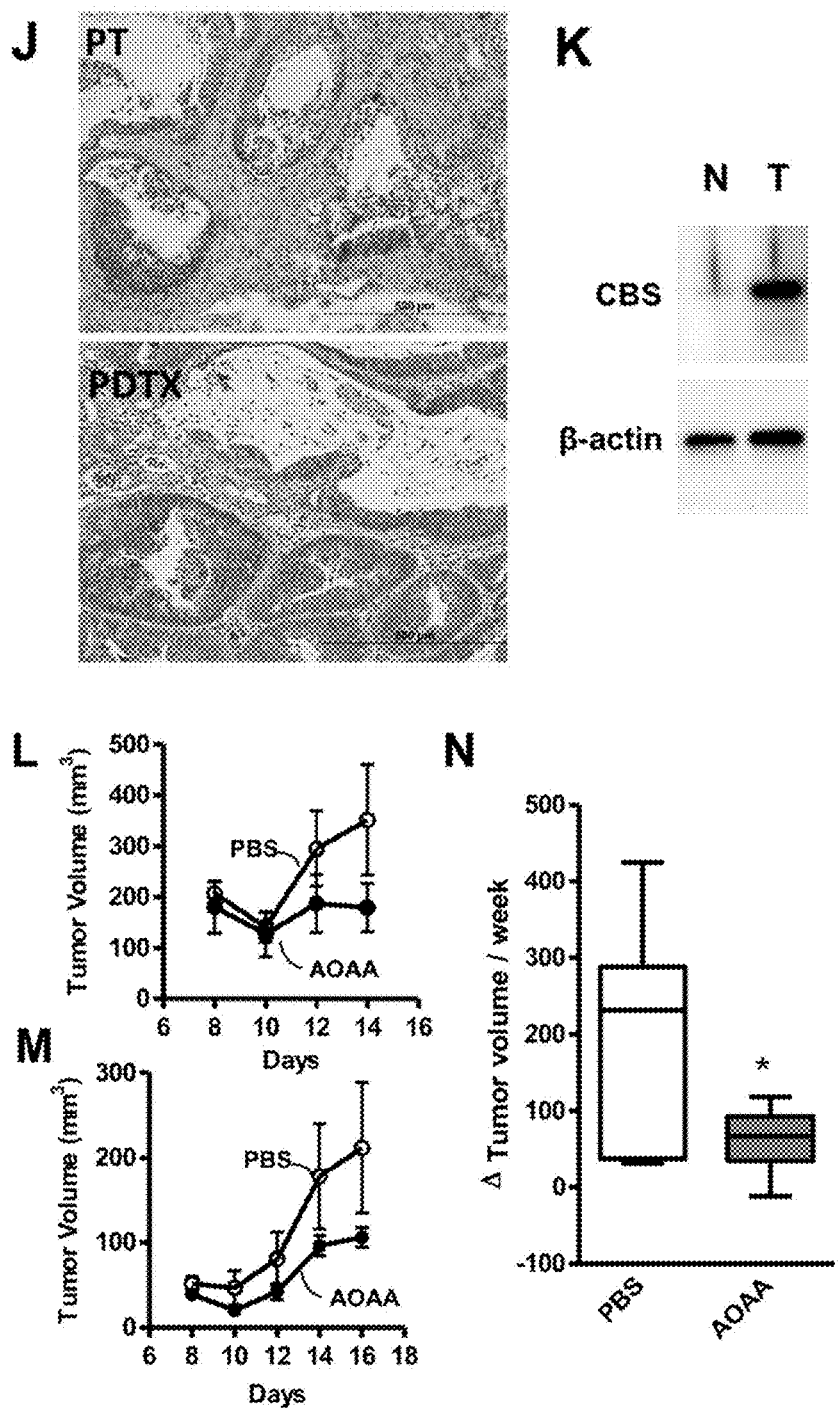

Both CBS silencing and AOAA (s.c. 9 mg/kg/day, QOD) suppresses tumor growth in a variety of in vivo colorectal tumor models (FIG. 5). In vivo tumor inhibition studies involve the subcutaneous xenografting of the colorectal cancer (CRC) cell lines and patient-derived colorectal tumor tissue into immune compromised mice. The potency of AOAA prodrugs in the inhibition of HCT116 xenograft growth is assessed. Based on recent studies using this model, a power analysis (Stata 8.1, College Station, Tex.) was performed with an alpha of 0.05 and a power of 0.93. Sample size calculations were based on a two-tailed ANOVA statistical test to detect a difference of one standard deviation between the vehicle (PBS) treated (negative control) vs. AOAA-treated (positive control) mice. The estimated sample size based on these calculations and criteria is 9 mice per group. In one example, each individual experiment will consist of 7 groups (63 mice total). group 1: negative control (i.e., s.c. PBS 100 μL, QOD), group 2-4: positive control (i.e., AOAA s.c. 9 mg/kg/day, QOD), and groups 5-7 (e.g., 3 different concentrations of AOAA prodrug s.c. 1, 3, 9 mg/kg/day, QOD).

Additional experiments determine the potency of AOAA prodrugs on a panel of PDTXs (Table 2). CBS-derived $H_2S$ supports mitochondrial electron transport and cancer cell bioenergetics by donating electrons at Complex II. By inhibiting CBS, AOAA suppresses this bioenergetic pathway. In addition, by inhibiting GOT, AOAA reduces the transfer of electron donors to the mitochondria, thereby suppressing cancer cell bioenergetics. By the simultaneous inhibition of CBS and GOT, AOAA interferes with two key pathways of cancer cell bioenergetics. For all in vivo tumorigenicity experiments, the effects of prodrug treatment on tumor growth rates are assessed over time (3-5 weeks) by transcutaneous measurement. At the end of each experiment, tumor tissue is harvested for bioenergetic analysis of mitochondria. (1) a proliferation index (i.e., Ki67-positive nuclei/total nuclei/high power field) by immunostaining, (2) a tumor apoptotic index [using TUNEL staining], and (3) tumor microvessel density by immunostaining for the endothelial cell surface marker CD31.

The protocol for PDTXs involves the engrafting of fresh early passage (<P4) PDTX tissue fragments into the needed number of mice. The estimated group size (10 animals/group) is based on a 50% treatment effect (with AOAA s.c. 9 mg/kg, QOD) in tumor size reduction. Once the average PDTX volume reaches approximately 0.3 $cm^3$, the mice are randomized into groups. The groups include: (1) vehicle control (positive control for maximum PTDX growth rate), (2) AOAA (up to three different concentrations), and (3) the AOAA prodrug (three different concentrations). PDTX growth rates are assessed over an eight-week time-course or until the subcutaneous tumors in the vehicle control group reach 10% of the mouse total body weight. In addition, PDTX tissue is subjected to detailed biochemical analysis (measurement of mitochondrial function, sulfhydration of GAPDH and PTEN and activation of the PI3K pathway etc.) In addition to the parameters of tumor growth, angiogenesis and ex vivo bioenergetics from mitochondria isolated from tumor tissues, plasma $H_2S$ and homocysteine levels are measured, as CBS inhibition in the liver could result in an elevation of circulating homocysteine levels. Finally, using the primary patient CRC tissue specimens (and surrounding non-malignant mucosa) and patient-matched PDTX before and after treatment, detailed immunohistochemical analyses is conducted in order to determine patient-to-patient variability in CBS expression as well as the localization of CBS expression within individual tumors/PDTXs (i.e., to determine whether the abundance of CBS is different in the ischemic core of the tumor vs. the highly vascularized and/or invasive areas etc), and whether the treatments effect either the overall levels of CBS expression or its tissue/cellular distribution within the PDTX.

TABLE 2

Colorectal cancer tissue information for our PDTX library. The information includes sex, age, KRAS status, differentiation grade, primary tumor stage (T), lymph node stage (N), metastasis status (M), cancer stage and primary tumor site, as shown.

| Patient | Sex | Age | KRAS | Differentiation | T | N | M | Stage | Site |
|---|---|---|---|---|---|---|---|---|---|
| 1 | M | 28 | Mutant | Grade 2 | T4 | N1b | | Stage 3 | sigmoid |
| 2 | F | 56 | Wild Type | Grade 1 | T3 | N1a | | Stage 3 | sigmoid |
| 3 | F | 70 | Mutant | Grade 2 | T2 | N0 | | Stage 2 | cecum |
| 4 | M | 87 | Unknown | Grade 3 | T3 | N2b | M1, spleen | Stage 4 | rectal |
| 5 | M | 49 | Mutant | Grade 1 | T3 | N0 | | Stage 2 | cecum |
| 6 | F | 52 | Wild Type | Grade 2 | T3 | N1b | | Stage 3 | sigmoid |

TABLE 2-continued

Colorectal cancer tissue information for our PDTX library. The information includes sex, age, KRAS status, differentiation grade, primary tumor stage (T), lymph node stage (N), metastasis status (M), cancer stage and primary tumor site, as shown.

| Patient | Sex | Age | KRAS | Differentiation | T | N | M | Stage | Site |
|---|---|---|---|---|---|---|---|---|---|
| 7 | M | 60 | Mutant | Grade 3 | T3 | N2b | M1, liver | Stage 4 | sigmoid |
| 8 | F | 72 | Wild Type | Grade 3 | T3 | N2b | | Stage 3 | cecum |
| 9 | M | 67 | Mutant | Grade 2 | T3 | N0 | | Stage2 | cecum |
| 10 | F | 57 | Mutant | Grade 1 | T3 | N0 | | Stage 2 | Right colon |
| 11 | M | 77 | Mutant | Grade 3 | T4 | N0 | | Stage 2 | cecum |

Based upon the in vitro and in vivo biological data profile of the AOAA prodrugs, compounds are selected for in vitro and in vivo pharmacokinetic studies. Compounds are evaluated in a permeability assay in Caco-2 cells. To avoid the potential liability of compound classes or individual compounds for cardiovascular side effects or inducing drug-drug interactions, hERG inhibition and CYP450 inhibition for the major human isoforms are assessed.

AOAA is currently the most potent known CBS inhibitor on human recombinant CBS that exerts inhibitory effects at low micromolar concentrations. However, in cell-based assays, its antiproliferative effects and its inhibitory effects on cellular energetics only manifests in higher (millimolar) concentrations (Szabo et al. Proc Natl Acad Sci USA. 110:12474-9, 2013). Since AOAA is a highly water-soluble molecule, it is hypothesized that the discrepancy between enzyme-based and cell-based potency of AOAA may be due to its limited cell uptake. The prodrug approach has been a common pharmacological way to improve the potency of compounds with limited cell membrane permeability (Rautio et al. Nat Rev Drug Discov. 7: 255-70, 2008). Appropriately selected prodrugs have improved cell membrane permeability; once inside the target cells, intracellular enzymes cleave off the prodrug moiety to give rise to the parent compound. To experimentally enable this concept for AOAA, the inventors have synthesized a series of AOAA prodrugs, including the AOAA methyl ester prodrug (termed YD-1-71). This compound, as well as several other examples of novel prodrugs (table 3) inhibited the proliferation of HCT116 cells at substantially lower concentrations than the parent compound AOAA. Based on these data, AOAA prodrugs shown in table 3 as well as the additional prodrugs shown in FIG. 10, are CBS inhibitors and anticancer compounds.

TABLE 3

| Compound name | Prodrug class | Structure | IC50 (µM) | % inhibition at 300 µM |
|---|---|---|---|---|
| AOAA | Parent compound | HO-C(=O)-CH2-O-NH2 | 1,783 | 21 |
| YD-1-71 | Methyl ester | CH3O-C(=O)-CH2-O-NH2 | 181 | 80 |
| YD-2-22 | Benzyl ester | PhCH2-O-C(=O)-CH2-O-NH2 | 159 | 91 |
| YD-2-23 | Carbamate | HO-C(=O)-CH2-O-NH-C(=O)-O-C(CH3)3 | 207 | 71 |

In certain embodiments a prodrug can have a chemical structure of Formula I,

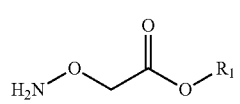

Formula I

In certain aspects $R_1$ of Formula I is a methyl, benzyl, or carbamate. In other aspects $R_1$ of Formula I is a ethyl (—CH$_2$CH$_3$), n-propyl (—CH$_2$CH$_2$CH$_3$), iso-propyl (—CH$_2$(CH$_3$)$_2$), n-butyl (—CH$_2$CH$_2$CH$_2$CH$_3$), sec-butyl (—CH(CH$_3$)CH$_2$CH$_3$) iso-butyl (—CH$_2$CH(CH$_3$)$_2$), tert-butyl (—C(CH$_3$)$_3$), n-pentyl (—CH$_2$(CH$_2$)$_3$CH$_3$), tert-pentyl (—CH(H$_3$C)$_2$CH$_2$CH3), neo-pentyl (—CH$_2$C(CH$_3$)$_3$), iso-pentyl (—CH$_2$CH$_2$CH(CH$_3$)$_2$), sec-pentyl (—CH(CH$_3$)CH$_2$CH$_2$CH$_3$), or 3-pentyl (—CH(CH$_2$CH$_3$)$_2$) group. In a still further aspect R1 of Formula I is a 3-pentyl group (YD-2-51).

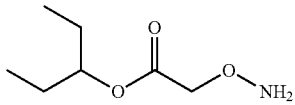

YD-2-51

III. PHARMACEUTICAL FORMULATIONS AND ADMINISTRATION

In certain embodiments, a patient is administered an anti-cancer agent in a composition comprising one or more of the following: a pharmaceutically acceptable diluent, a carrier, a solubilizer, an emulsifier, a preservative, and/or an adjuvant. Such compositions may contain an effective amount of at least one anti-cancer agent. In certain aspects the anti-cancer agent is a cystathionine-β-synthase (CBS) inhibitor. In another aspect, the anti-cancer agent is a hydrogen sulfide neutralizing agent. Thus, the use of one or more anti-cancer agents that are provided herein in the preparation of a pharmaceutical composition of a medicament is also included. Such compositions can be used in the treatment of a variety of cancers associated with elevated H$_2$S production. In certain embodiments the treatment is for colorectal cancer.

The anti-cancer agents may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The formulation will depend upon the mode of administration and the particular cancer target. The compositions may also include pharmaceutically acceptable vehicles, carriers, or adjuvants known in the art.

In addition to the anti-cancer agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a catheter. Local administration to a tumor in question is also contemplated by the present invention. When administering the compositions by injection, the administration may be by continuous infusion or by single or multiple boluses. For parenteral administration, the anti-cancer agents may be administered in a pyrogen-free, parenterally acceptable aqueous solution comprising the desired anti-cancer agent(s) in a pharmaceutically acceptable vehicle. A particularly suitable vehicle for parenteral injection is sterile distilled water in which one or more anti-cancer agents are formulated as a sterile, isotonic solution.

Once the pharmaceutical composition of the invention has been formulated it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

For the compounds of the present invention, alone or as part of a pharmaceutical composition, such doses are between about 0.001 mg/kg and 1 mg/kg body weight, preferably between about 1 and 100 µg/kg body weight, most preferably between 1 and 10 µg/kg body weight. Therapeutically effective doses will be easily determined by one of skill in the art and will depend on the severity and course of the disease, the patient's health and response to treatment, the patient's age, weight, height, sex, previous medical history and the judgment of the treating physician.

In some methods of the invention, the cancer cell is part of a tumor. The cancer cell may be in a patient. The patient may have a solid tumor comprising cancer cells. In such cases, embodiments may further involve performing surgery on the patient, such as by resecting all or part of the tumor. Compositions may be administered to the patient before, after, or at the same time as surgery. In additional embodiments, patients may be administered anti-cancer agents directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

In some embodiments, the composition(s) described herein are administered to a cancer that exhibits an elevated production rate of hydrogen sulfide. Alternatively, the cancer may exhibit an elevated expression of CBS. In certain aspects CBS activity can be determined by assays such as those described in Chen et al., (2004) *J Biol Chem*, 279(50): 52082-86. Briefly, CBS enzyme activity assays include, but are not limited to three different assays. Native gel assays can detect $H_2S$ production by reaction with Pb-acetate. Protein samples can be electrophoresed on native gels and active protein bands can be detected by soaking the gel in a reaction assay mixtures (e.g., 200 mM Na/Bicine (pH 8.6), 50 mM PLP, 0.25 mg/ml bovine serum albumin, 0.4 mM Pb-acetate and substrates, such as L-cysteine/L-homocysteine, L-cysteine/2-mercaptoethanol, or L-cysteine). Spectrophotometric assays can be used to detect $H_2S$ production from CBS. The reaction of $H_2S$ with lead acetate forms lead sulfide, which can be monitored continuously by the increase in absorbance at 390 nm. Enzyme activity can also be measured using a reaction containing 100 mM Na-Bicine, pH8.6, 200 mM PLP, 1 mM TCEP, 100 mM AdoMet, 0.25 mg/ml BSA and 10 mM L-homocysteine. The concentrations of co-substrates serine or cysteine can be up to 40 mM. Cystathionine production can be measured by using an amino acid analyzer (e.g., Biochrom 30).

In certain aspects the cancer is colorectal cancer. Without being bound by theory, it is believed that the CBS inhibitors are particularly effective in colorectal cancer due to the unique bacterial environment of the colon. Sulfur-producing bacteria are more prevalent in the colon, thus requiring colorectal epithelial cells to adapt to increased concentrations of $H_2S$.

IV. METHODS OF GENOTYPING

A variety of means can be used to genotype an individual at a polymorphic site in an oncogene such as the Kras gene to determine whether a sample (e.g., a nucleic acid sample) contains a specific variant allele (e.g., somatic mutation) or haplotype. For example, enzymatic amplification of nucleic acid from an individual can be conveniently used to obtain nucleic acid for subsequent analysis. The presence or absence of a specific variant allele (e.g., somatic mutation) or haplotype in one or more oncogenes of interest can also be determined directly from the individual's nucleic acid without enzymatic amplification. In certain embodiments, an individual is genotyped at one, two, three, four, five, or more polymorphic sites such as a single nucleotide polymorphism (SNP) in one or more oncogenes of interest.

Genotyping of nucleic acid from an individual, whether amplified or not, can be performed using any of various techniques. Useful techniques include, without limitation, assays such as polymerase chain reaction (PCR) based analysis assays, sequence analysis assays, electrophoretic analysis assays, restriction length polymorphism analysis assays, hybridization analysis assays, allele-specific hybridization, oligonucleotide ligation allele-specific elongation/ligation, allele-specific amplification, single-base extension, molecular inversion probe, invasive cleavage, selective termination, restriction length polymorphism, sequencing, single strand conformation polymorphism (SSCP), single strand chain polymorphism, mismatch-cleaving, and denaturing gradient gel electrophoresis, all of which can be used alone or in combination. As used herein, the term "nucleic acid" includes a polynucleotide such as a single- or double-stranded DNA or RNA molecule including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

V. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice.

However, those of skill in the art should, in light of the present disclosure, appreciate that many changes can be made in the specific embodiments which are disclosed and still obtain a like or similar result without departing from the spirit and scope of the invention.

Example 1

Cystathionine-B-Synthase (CBS)-Derived Hydrogen Sulfide ($H_2S$) Supports Cellular Bioenergetics in Colon Cancer Cells In Vitro A. Results CBS is Overexpressed in Human Colon Adenocarcinomas.

Comparison of human colon cancer specimens with patient-matched normal mucosa tissue revealed the selective upregulation of the $H_2S$-producing enzyme cystathionine-β-synthase (CBS) in the cancers (FIGS. 1A and 1B). In contrast, the expression of the other two $H_2S$-producing enzymes, cystathionine-γ-lyase (CSE) and 3-MST remained unchanged (FIG. 1A). Similar to colon tumors, colon adenocarcinoma-derived cell lines (HCT-116, HT-29, LoVo) exhibited the selective upregulation of CBS, when compared to the non-malignant colonic epithelial cell line (NCM356) (FIGS. 1C and 1D). Homogenates of the patient-derived colon tumor specimens, as well as homogenates of the colon cancer-derived cell lines exhibited increased rates of $H_2S$ production (FIGS. 1E and 1F).

CBS is Associated with Colon Cancer Cell Mitochondria.

Figure 2:
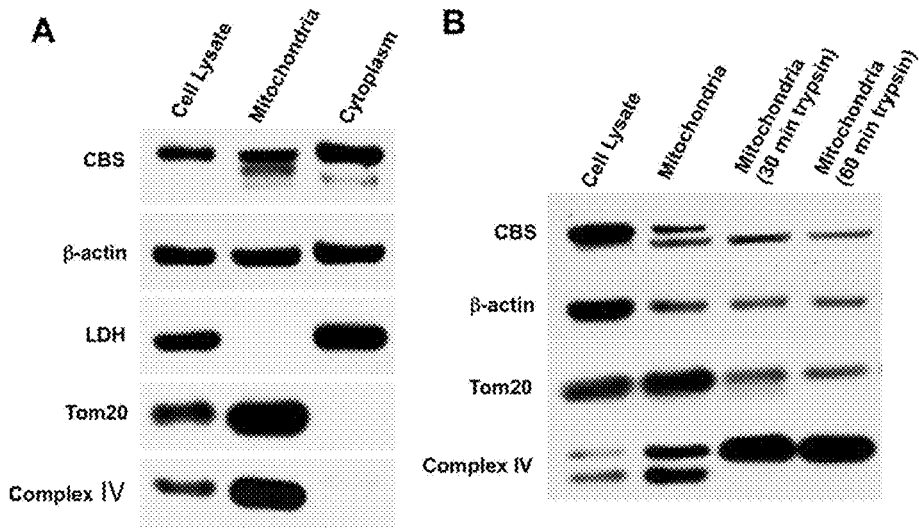
FIG. 2. Presence of CBS in cytosolic and mitochondrial fractions of HTC116 cells. (A) CBS was detected in whole cell lysates as well as in mitochondrial and cytoplasmic cell fractions harvested from HTC116 cells. (B) Limited trypsin digestion of isolated mitochondria (30-60 min) reduced mitochondrial CBS, as well as the mitochondrial outer membrane protein Tom20, while enriching complex IV (an inner membrane protein). Each Western blot is representative of at least three independent experiments.

Cell fractionation studies showed that a significant portion of the total amount of cellular CBS was associated with the mitochondria in HCT116 cells (FIG. 2A). A trypsin digestion assay on isolated mitochondria (FIG. 2B), showed that CBS was primarily associated with the outer mitochondrial membrane.

CBS-Derived $H_2S$ Stimulates Colon Cancer Cell Proliferation, Migration, and Invasion In Vitro.

Figure 3:
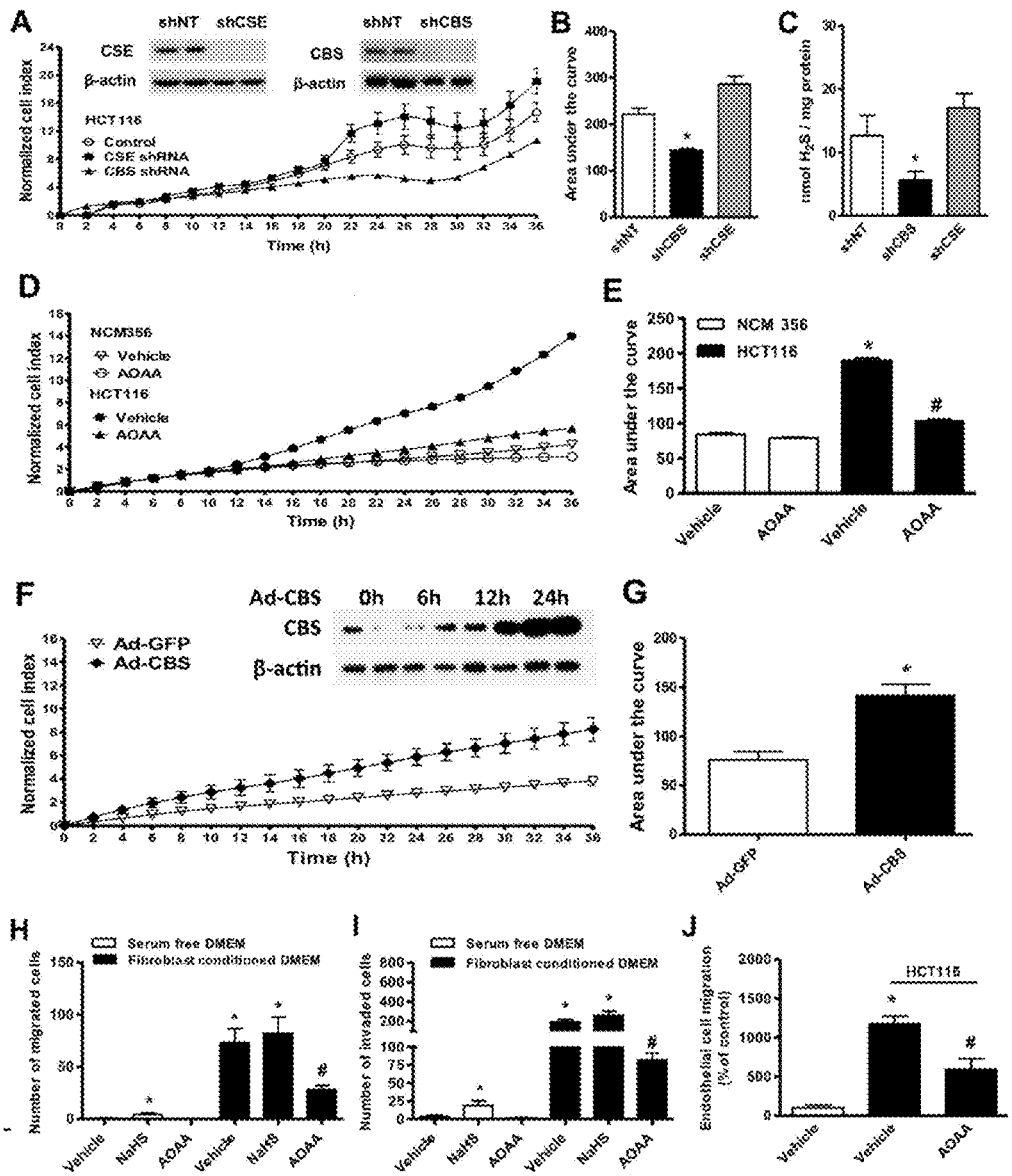
FIG. 3. ShRNA mediated down-regulation of CBS or pharmacological inhibition by AOAA inhibits proliferative, migratory, and invading activity of HCT116 cells in vitro. (A, B) The lentiviral shRNA vectors targeting CBS (shCBS) and CSE (shCSE) were transfected into HCT116 cells. A non-targeting sequence was used as control (shNT). The shRNA approach inhibited the expression of both CBS and CSE gene at the protein level, as shown by western blotting (inset). Following CBS and CSE silencing, cells were seeded at the density of 3000 cells/well in xCELLigence plates and proliferation was monitored for 36 hours. Down-regulation of CBS, but not of CSE, significantly reduced HCT-116 proliferation rate ($*p<0.05$ vs. shNT). (C) shCBS but not shCSE yielded lower $H_2S$ production in cellular homogenates ($p<0.05$ vs. shNT). (D, E) HCT116 cells exhibited a significantly higher proliferation rate, compared to NCM356 cells. AOAA (1 mM) did not affect NCM356 growth, but markedly reduced HCT116 cell proliferation ($*p<0.05$ vs. NCM356 and $\#p<0.05$ vs. vehicle). (F, G) Adenoviral mediated CBS overexpression enhances the proliferation rate of NCM356 cells. The NCM356 cells were infected overnight with a CBS expressing adenovirus (Ad-CBS, 10 multiplicity of infection (MOI)) or its control, a green fluorescent protein (Ad-GFP). The culture media was then replaced and cells were seeded in XCelligence plates at 3000 cells/well. Cell proliferation was then measured real-time over 36 hours. Effective overexpression of CBS was detected within 12-24 hours following infection (inset). Adenoviral mediated CBS overexpression significantly enhanced NCM356 cell proliferation ($*p<0.05$ vs. Ad-GFP). (H, I) The effect of AOAA and NaHS was also tested on HCT116 cell migration (H) and invasion (I). Cells were pretreated either with vehicle or AOAA (1 mM) and seeded in serum-free DMEM (0.1% albumin) in the upper chamber of a trans-well insert uncoated (migration assay) or coated with growth factor reduced matrigel (invasion assay). Migration and invasion were stimulated by fibroblast-conditioned media in the lower chamber for 6 and 24 hours, respectively. NaHS (30 μM) in the lower chamber slightly enhanced HCT116 cell migration and invasion in serum-free media. AOAA markedly reduced fibroblast derived growth factor-induced HCT116 cell migration and invasion ($*p<0.05$ and $\#p<0.05$). (J) In a co-culture of human endothelial cells (EAhy926) and colon cancer cells (HCT116), HCT 116 cells were seeded in the lower chamber of a trans-well insert and cultured to confluence. Endothelial cells were then seeded into the upper chamber in serum-free DMEM and allowed to migrate for 4 hours at 37° C. The presence of HCT116 in the lower chamber markedly increased the number of migrated endothelial cells, and this effect was reduced by AOAA ($*p<0.05$). Western blots are representative of at least three independent experiments; proliferation/migration/invasion assays and $H_2S$ measurements represent mean±SEM of n=3 determinations.

Gene specific short-hairpin RNA (shRNA) sequences in lentiviral vectors were used to suppress the expression of either CBS or CSE in HCT116 cells (FIG. 3A). Densitometric analyses of Western blots revealed an approximately 50% decrease in CBS expression with comparable reductions in both cell proliferation (FIGS. 3A and 3B) and $H_2S$ production (FIG. 3C). In contrast to CBS, silencing of CSE did not significantly affect either HCT116 cell proliferation or $H_2S$ production (FIGS. 3A, 3B, and 3C). To further define the function of CBS in colon cancer cells, the inventors treated both NCM356 (which express CSE, but only low levels of CBS, FIG. 1C), and HCT116 cells (which overexpress CBS) with the pharmacological CBS inhibitor, aminooxyacetic acid (AOAA). Consistent with the CBS knockdown experiments, AOAA treatment inhibited the growth of HCT116 colon cancer cells, but did not affect the proliferation of the slower-growing non-malignant NCM356 cell line (FIGS. 3D and 3E). Conversely, forced overexpression of CBS in NCM356 cells significantly increased their basal rate of proliferation (FIGS. 3F and 3G). AOAA treatment also suppressed the migration (FIG. 3H) and invasion (FIG. 3I) of HCT116 cells. Inhibition of CBS with AOAA reduced endothelial cell migration in colon cancer/endothelial cell co-cultures (FIG. 3J).

CBS-Derived $H_2S$, Produced by Human Colon Cancer Cells, Stimulates Cancer Cell Bioenergetics In Vitro.

Figure 4:
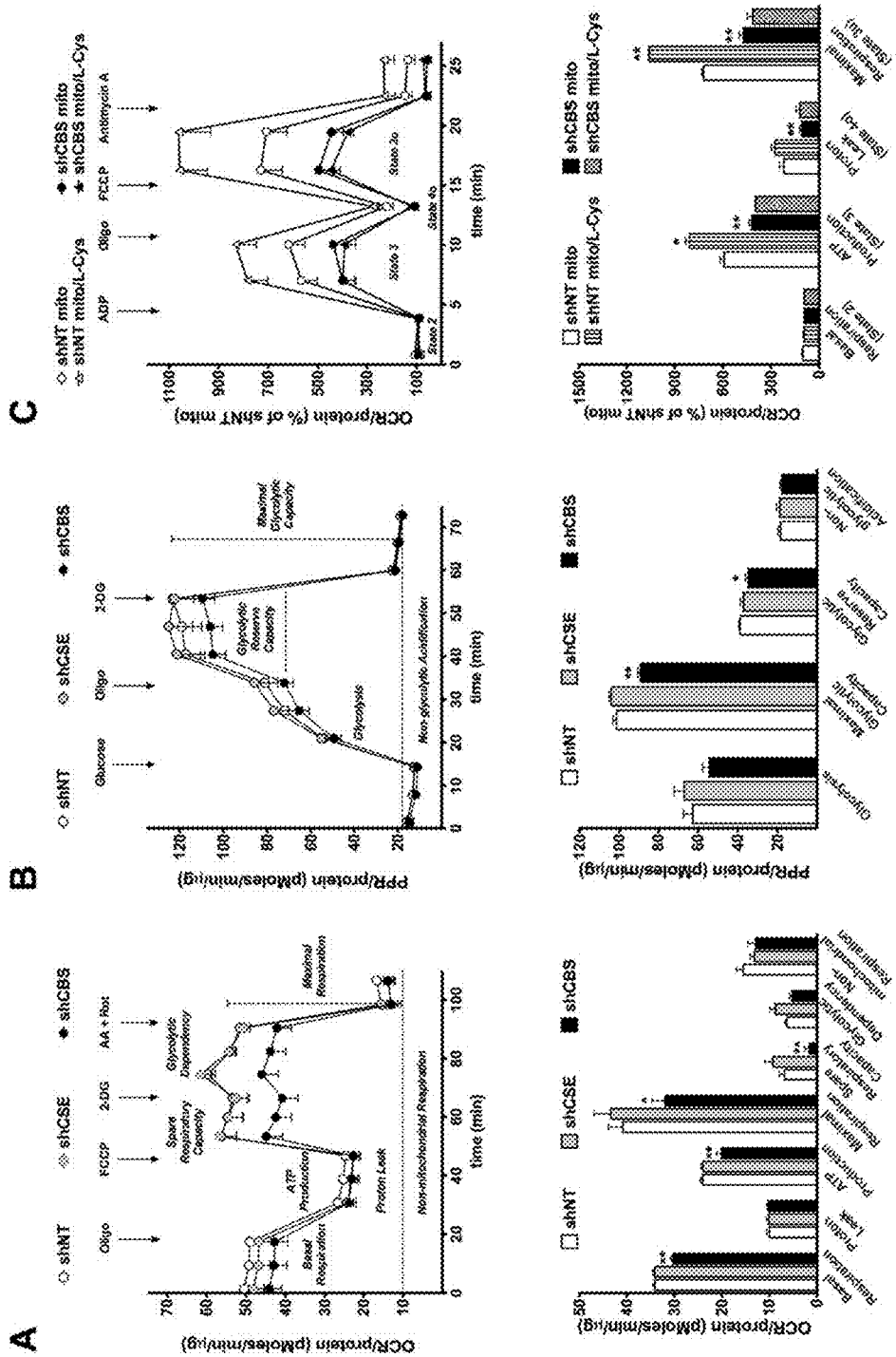
FIG. 4. ShRNA mediated down-regulation of CBS suppresses cellular bioenergetics in HTC116 cells. (A) Oxygen consumption rate (OCR) in HTC116 cells subjected to either non-targeting (shNT, control) or stable lentiviral silencing of CBS or CSE (shCBS, shCSE). shCBS enzyme significantly decreased basal OCR, calculated ATP production, maximal respiration and Spare Respiratory Capacity ($*p<0.05$ or $**p<0.01$ vs. shNT), while CSE silencing had no effect on the bioenergetic profile. (B) shCBS significantly diminished the maximal glycolytic capacity and the glycolytic reserve capacity ($*p<0.05$ or $**p<0.01$ vs. shNT), while CSE silencing had no effect on the glycolytic parameters. (C) Coupling experiments show that L-cysteine (30 nM) elevates OCR in state 3 and state 3u respiration in mitochondria isolated from control shNT cells ($*p<0.05$), but not in mitochondria isolated from shCBS cells ($\#p<0.05$ or $\#\#p<0.01$). Data represent mean±SEM of n=4-5 determinations.
Figure 7:
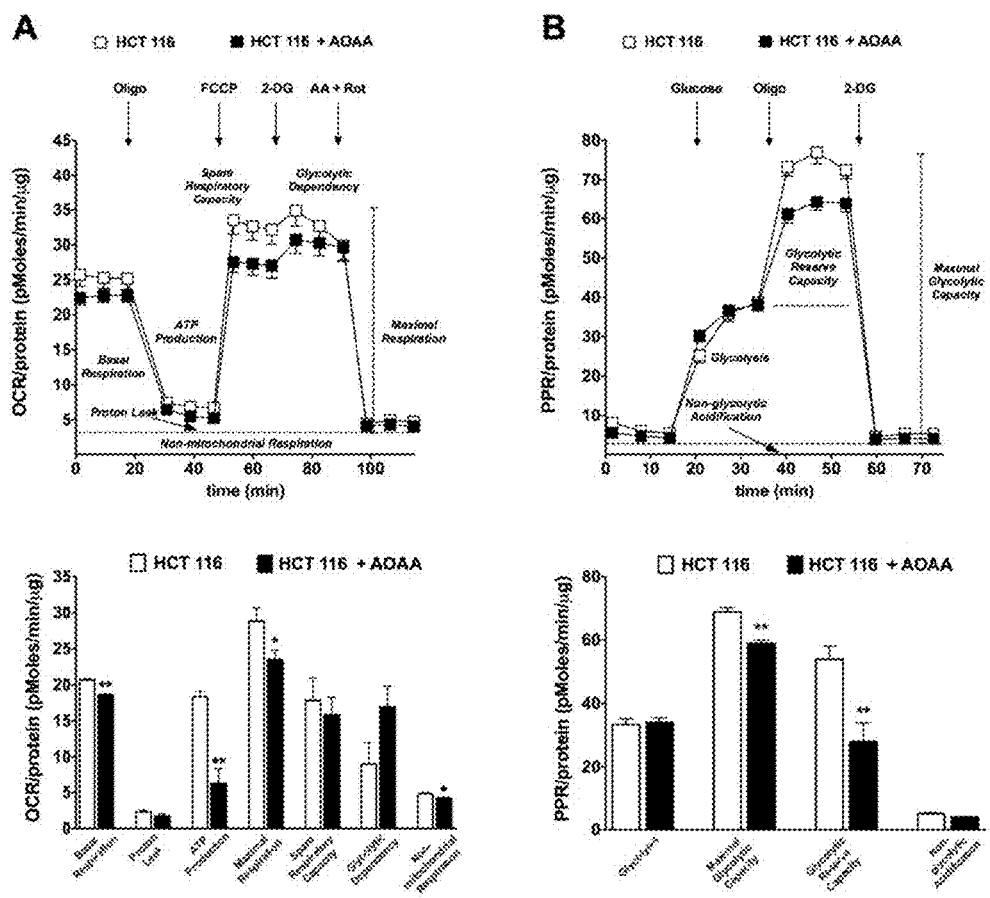
FIG. 7. AOAA suppresses cellular bioenergetics in HTC116 cells. (A) Oxygen consumption rate (OCR) in HTC116 cells subjected to vehicle or AOAA (1 mM). AOAA significantly decreased basal OCR, calculated ATP production, maximal respiration and Spare Respiratory Capacity (*p<0.05 or **p<0.01). (B) AOAA significantly diminished the maximal glycolytic capacity and the glycolytic reserve capacity (*p<0.05 or **p<0.01). Data represent mean±SEM of n=3 determinations.

In agreement with the physiological role of endogenous $H_2S$ in promoting cellular bioenergetics (Goubern et al. (2007) *FASEB J* 21:1699-1706; Módis et al. (2013) *FASEB J* 27:601-11), shRNA-mediated knockdown of CBS (but not of CSE) expression, or CBS inhibition with AOAA reduced basal cellular respiration, suppressed the calculated ATP synthesis, and attenuated the spare respiratory capacity (FIG. 4A, FIG. 7). CBS silencing or CBS inhibition also reduced glycolytic functions (FIG. 4B, FIG. 7). This effect may be attributed, at least in part, to inhibition of GAPDH activity: GAPDH activity was quantified in HCT116 cells, and it was reduced by CBS silencing. (GAPDH activity in wild-type and CBS silenced cells amounted to 6.2±0.2 U/ml and 4.0±0.1 U/ml, respectively, n=3, p<0.01). In mitochondria prepared from HCT116 cells, L-cysteine stimulated mitochondrial electron transport; this effect was absent in mitochondria prepared from shCBS cells expression (FIG. 4C).

CBS Stimulates Tumor Xenograft Growth, Angiogenesis, and Peritumoral Vascular Tone.

Consistent with the in vitro findings, shRNA-mediated knockdown of CBS expression significantly reduced the growth rate and size (i.e., volume) of HCT116 tumor xenografts (FIGS. 5A and 5B). In contrast, silencing of CSE did not affect tumor growth (FIGS. 5A and 5B). Silencing of CBS or CSE in the tumor cells did not alter circulating $H_2S$ levels in tumor-bearing mice (FIG. 5C).

CBS suppression caused a significant reduction in the density of CD31-positive blood vessels within the tumor tissue (FIG. 5D) as well as the prevalence of larger blood vessels and the extent of vessel branching (FIG. 5E), consistent with the hypothesis that CBS-derived $H_2S$ acts locally in a paracrine manner to stimulate tumor angiogenesis.

Figure 6:
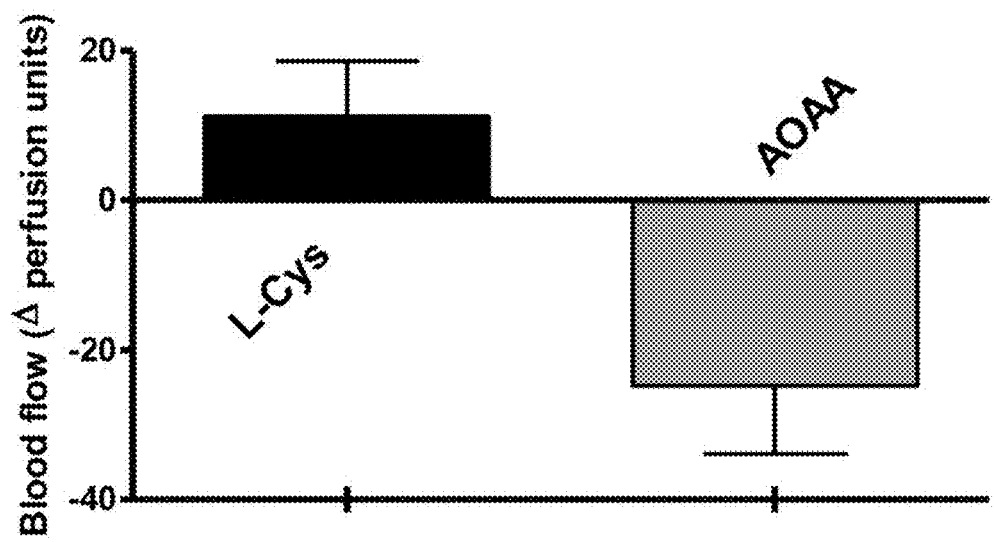
FIG. 6. L-Cysteine increases, while AOAA reduces microvessel blood flow in tumor bearing mice. Tumor bearing mice were anesthetized by i.p. injection of ketamine-xylazine and a laser Doppler (PeriFlux system 5000) was placed on top of the tumor for microvessel blood flow measurements. After a stabilization period, L-Cys or AOAA were injected subcutaneously in proximity of the tumor. AOAA caused a marked decrease of the skin microvessel blood flow. Data represent mean±SEM of n=6 determinations.

Since small-molecule inhibitors are potentially more amenable to therapeutic translation than shRNA-based strategies, the inventors tested the effects of small molecule CBS inhibitor, represented by AOAA, on tumor growth in vivo. Similar to CBS knockdown, AOAA treatment significantly slowed the rate of HCT116 xenograft growth (FIG. 5F), resulting in tumors with reduced size and weight at the time of harvest (FIGS. 5G and 5H). A reduction in the plasma concentration of $H_2S$ confirmed the inhibitory effect of AOAA on systemic $H_2S$ production (FIG. 5I). Also, in accordance with the role of $H_2S$ as a local vasodilator, direct injection of AOAA into the tumor parenchyma significantly reduced, while intra-tumor administration of the CBS substrate L-cysteine increased peritumor flow (FIG. 6).

The patient-derived tumor xenograft (PDTX) is an emerging preclinical model for anti-cancer drug development, because it more closely recapitulates both the genetic and cellular heterogeneity of the patient's original tumor tissue (Tentler et al. (2012) *Nat Rev Clin Oncol.* 9:338-50) (FIG. 5J). To begin testing the concept that CBS inhibition could be an effective strategy for future therapeutic development, the inventors evaluated the effects of AOAA treatment on mice bearing PDTXs derived from the primary adenocarcinoma of a patient with pathological stage III disease with an activating Kras mutation and with a marked overexpression of endogenous CBS (FIG. 5K). Following randomization, xenograft-bearing mice were treated daily either with AOAA or vehicle (PBS). AOAA-treated animals showed a reduced rate of PDTX growth (FIG. 5L). Importantly, the growth inhibitory effects of AOAA on PDTX growth were also observed using tumor tissue from a second patient with stage II disease that also possessed a mutant Kras allele (FIG. 5M). Summary data from two independent experiments using the PDTXs from the different patients showed that AOAA effectively reduced the rate of PDTX growth over the time course of the treatment (FIG. 5N).

B. Methods

Collection and Analysis of Samples from Human Colon Cancers.

Freshly resected human colorectal tumor tissue, along with a specimen of patient-matched normal mucosa (wide margin), was collected under an IRB approved protocol and snap frozen in liquid $N_2$. Clinico-pathologic information of samples collected is provided in table 4.

TABLE 4

| Patient sample | Age | Sex | Stage |
| --- | --- | --- | --- |
| 1 | 66 | F | Normal margin of Stage III |
| 2 | 60 | M | Normal margin of stage III |
| 3 | 63 | F | Normal margin of adenoma |
| 4 | 47 | F | Chronic inflammation |
| 5 | 30 | M | Stage II |
| 6 | 63 | F | Adenoma |
| 7 | 78 | F | Stage II |
| 8 | 88 | F | Stage II |
| 9 | 75 | M | Stage II |
| 10 | 28 | M | Stage III |

Colon Cancer Cell Lines.

The colon cancer cell line HT-29 (ATCC, Manassas, Va.) and the non-tumorigenic colon epithelial cell line derived from the normal margin of a rectal cancer specimen, NCM356 (Suzuki et al. (2011) *Proc Natl Acad Sci USA* 108:13829-34) were cultured in DMEM supplemented with 10% fetal bovine serum. HCT-116 and LoVo cells (ATCC) were cultured in McCoy's 5A and F-12, respectively.

Subcellular Fractionation and Western Blotting for CBS.

HTC116 cells were subjected to subcellular fractionation by centrifugation (Frezza et al. (2007) *Nat Protoc.* 2:287-95). Mitochondrial and cytosolic fractions were analyzed by Western blotting; membranes were probed overnight with anti-CBS (60 kDa), anti-β-actin (43 kDa), anti-LDH (35 kDa), anti-Tom20 (20 kDa) and anti-Complex IV (17 kDa) antibodies. In a separate set of experiments, the mitochondrial outer membrane was subjected to limited trypsin digestion (Szczesny et al. (2003) *Proc Natl Acad Sci USA.* 100:10670-75), followed by Western blotting.

$H_2S$ Measurement in Plasma and Cell Lysates.

For detection of L-cysteine-induced $H_2S$ production in cell lysates, or for the measurement of plasma levels of $H_2S$, the methylene blue assay was used (Módis et al. (2013) *FASEB J.* 27:601-11; Suzuki et al. (2011) *Proc Natl Acad Sci USA* 108:13829-34).

ShRNA-Mediated Silencing of CBS and CSE and Adenoviral Mediated Overexpression of CBS.

Colon cancer cell lines were transduced with either a lentiviral vector containing shRNA sequences targeting CBS (SHCLNV, clone TRCN0000045359) or shCSE (clone TRCN0000078263). A non-targeting control shRNA sequence (shNT) was used to control of off-target effects (SHC002V, MISSION shRNA, Sigma-Aldrich; St. Louis, Mo.). HCT116 cells were infected at a MOI of 3 with hexadimethrine bromide (8 μg/ml). Transduced cells were selected and maintained in McCoy's 5A media supplemented with 10% FBS and Puromycin (2 μg/ml)(Kim et al. (2012) *J Biol Chem.* 287:33377-88). To overexpress CBS in the normal colon mucosa cell line NCM356, gene transfer was accomplished using an adenovirus at a MOI of 10, with a green fluorescent protein-expressing adenovirus used as a control (Suzuki et al. (2011) *Proc Natl Acad Sci USA* 108:13829-34). shRNA sequences for CBS include, but are not limited to CCGGCTTGCCAGATATTCT-GAAGAACTCGAGTTCTTCAGAATATCTG-GCAAGTTT TTG (SEQ ID NO:1 (Clone Number TRCN0000045360, Sigma) and CCGGGCGGAACTACAT-GACCAAGTTCTCGAGAACTTGGTCATGTAGTTC-CGCTTTTT G (SEQ ID NO:2 Clone Number TRCN0000045359, Sigma).

Proliferation, Migration, Invasion and Endothelial Cell Proliferation Assays In Vitro.

Cellular migration and invasion assays were performed as described (Chao et al. (1996) *Cancer Res.* 56:4811-19). Briefly, $10^5$ cells were suspended in serum-free media containing 0.1% BSA and then added to 6.5 mm Transwell chambers (8 mm pore) uncoated (migration assay) or coated with a thin layer (45 μl) of growth factor reduced matrigel (cell invasion assay). Cells were allowed to migrate toward the bottom chamber containing fibroblast (NIH-3T3 cells) conditioned media at 37° C. for 6 or 24 h for cell migration and invasion, respectively. Migrated and invaded cells were then fixed in Carson's fixative, stained in 0.33% toluidine blue and quantified by visual counting. For the HCT116-EAhy926 co-culture experiment, the cancer cell line was grown to confluence in the bottom wells of the transwell chambers and then endothelial cell migration was assessed (Coletta et al. (2012) *Proc Natl Acad Sci USA.* 109:9161-66). For assessment of colon cell proliferation, the xCELLigence system (Roche) was used (Szabo and Papapetropoulos (2011) *Br J Pharmacol.* 164:853-65).

Bioenergetic Analysis in Intact Cells.

The XF24 Extracellular Flux Analyzer (Seahorse Bioscience, Billerica, Mass.) was used to measure bioenergetic function as described in Módis et al. ((2013) *FASEB J* 27:601-11) and Wu et al. ((2007) *Am J Physiol Cell Physiol.* 292:C125-36). Oxygen consumption rate (OCR) after oligomycin (1.5 μg/ml) was used to assess ATP production rate and OCR after FCCP (0.5 μM) to assess maximal mitochondrial respiratory capacity. 2-deoxyglucose (100 mM) was used to estimate cellular glycolytic dependency and antimycin A (2 μg/m) and rotenone (2 μM) were used to inhibit the flux of electrons through complex III and I, to detect residual non-mitochondrial activity. For the measurement of glycolytic parameters, the changes in proton production rate (PPR) were monitored in response to the sequential administration of D-glucose (10 mM), oligomycin (1.5 μM) and 2-deoxyglucose (100 mM), to assess glycolysis, maximal glycolytic capacity, glycolytic reserve capacity, and non-glycolytic acidification rate, respectively. GAPDH activity was determined by a kinetic assay (ScienCell, Carlsbad, Calif.).

Bioenergetic Analysis in Isolated Mitochondria.

Bioenergetic measurements in mitochondria isolated from shNT and shCBS HCT-116 cells were conducted in the absence or presence of L-cysteine (30 nM) (Módis et al. (2013) *FASEB J* 27:601-11; Wu et al. (2007) *Am J Physiol Cell Physiol.* 292:C125-36). Basal respiration (State 2) in the presence of succinate and rotenone was measured, followed by State 3 (phosphorylating respiration), in the presence of ADP. State 4o was determined after the addition of oligomycin, and maximal uncoupler-stimulated respiration (State 3u) was assessed in the presence of FCCP.

Human Tumor Xenograft Studies in Immune Compromised Mice.

Nu/nu Balb/C female mice (8-10 weeks) were injected subcutaneously in the right and left dorsum ($10^6$ cells/side with HCT-116 cells). One week later, the mice were randomized and subcutaneous injections of phosphate buffered saline (PBS) or AOAA (9 mg/kg/day) were performed 6 days/week. Tumor diameters were measured transcutaneously using calipers and tumor volumes were calculated using the formula $V=(\pi/6)hd^2$. T-test comparisons of the tumor volumes and final weights at harvest were performed. Xenotrials with patient-derived xenografts (PTX) were performed on nu/nu mice implanted subcutaneously with a piece of Passage 2 tumor measuring 2-5 mm³ each. When a small palpable tumor was evident at 7-10 days, the mice with tumor take were randomized and subjected to subcutaneous injection of vehicle or AOAA (9 mg/kg/day) 6 days/week. Specimens were fixed with 10% formalin and embedded in paraffin. 5 µm sections were stained with hematoxylin and eosin. Each in vivo experiment was repeated at least twice.

Quantification of Blood Vessel Density.

Tissue preparation, immunostaining of CD31, and evaluation of microvessel density with the Chakley reticle was performed as described (Chao et al. (1996) *Cancer Res.* 56:4811-19).

Measurement of Microvascular Blood Flow.

Skin microvascular blood flow was measured using a PeriFlux 5000 laser-Doppler flowmeter. Mice bearing PTX were anesthetized by ketamine-xylazine (i.p.). The laser-Doppler probe was placed on top of the tumors and a stable basal signal was recorded. Changes in the subcutaneous microcirculatory perfusion were detected following intratumoral injections of either L-cysteine (1 mg/kg) or AOAA (9 mg/kg).

Statistical Analysis.

All data are presented as means±SEM and were analyzed using GraphPad Prism software. Statistical analyses included Student-t test or one-way ANOVA followed by Bonferroni's multiple comparisons.

Example 2

Identification of CBS Inhibitors

Human recombinant CBS is expressed as described (Asimakopoulou et al, (2013) *Br J Pharmacol.* 169(4):922-32). A library of pharmacologically active compounds (e.g., LOPAC library, Sigma; 1240 compounds) is tested on homocysteine-induced $H_2S$ production. In certain aspects the assay is in a 96-well format. In certain aspects $H_2S$ production is measured by the methylene blue assay (Asimakopoulou et al., (2013) *Br J Pharmacol.* 169(4):922-32). An example of CBS inhibitors identified using such a screen is provided in table 1 above, which shows a listing of CBS inhibitors identified from the LOPAC library.

Plasmids, bacterial strains and media. *E. coli* BL21 (DE3) Codon Plus is used as a host strain to express recombinant human CSE or CBS. CSE cDNA was cloned into pGEX-4T3 and CBS into pGEX-Kg to create N-terminal GSH-S-transferase (GST) fusion proteins. The expression vectors were transformed and plated on LB-agar plates, supplemented with ampicillin (100 µg/mL).

Protein Expression and Purification.

The expression and purification of CSE and CBS is performed as described previously with modifications (Frank et al., (2008) *Arch Biochem Biophys* 470:64-72; Huang et al., (2009) *J Mol Biol* 396: 708-18). Briefly, BL21(DE3) Codon Plus cells containing either the expression vector pGEX-4T3/GST-CSE or pGEX-Kg/GST-CBS are grown at 37° C. and 180 r.p.m. in LB broth medium containing 100 µg/mL ampicillin to an absorption of 0.6-0.8 at 600 nm. In addition, 0.3 mM d-ALA is added to the culture containing pGEX-Kg/GST-CBS. Then protein expression is induced by addition of 0.1 mM IPTG. Cells containing pGEX-4T-3/GST-CSE are incubated overnight at 18° C., whereas cells containing pGEXKg/GST-CBS are incubated overnight at 30° C. Culture is then centrifuged at 4° C. and 5000×g for 10 min and the cell pellet was resuspended in PBS (140 mM NaCl, 2.7 mM KCl, 10 mM $Na_2HPO_4$, 1.8 mM $KH_2PO_4$, pH 7.8) and stored at −20° C. overnight. After thawing, the suspension is sonicated in lysis buffer containing PBS and protease inhibitor cocktail for GST-CSE and PBS, 5 mM DTT, 1% Triton X-100, 100 mM PLP and protease inhibitor cocktail for GST-CBS. After centrifugation at 4° C. for 30 min, the soluble fraction containing either the GST-CSE or the GST-CBS recombinant protein is loaded onto a GSTrap FF 1 mL affinity column that has been equilibrated with binding buffer PBS. The column was consecutively washed with five column volumes of binding buffer. Proteins attached to the column, including GST-CSE or GST-CBS recombinant proteins, are eluted with five column volumes of elution buffer (50 mM Tris-HCl, 10 mM reduced GSH, pH 8.0) and then dialysed and concentrated in 10 mM sodium phosphate buffer pH 8.2 and DTT 1 mM. The purity of the recombinant enzymes was checked by SDS-PAGE on 12% polyacrylamide gels after staining of protein bands with Coomassie Blue R-250. Protein concentration was determined using the DC protein assay kit.

Measurement of $H_2S$ Production (Methylene Blue Assay).

$H_2S$ determination is performed according to Stipanuk and Beck ((1982) *Biochem J* 206:267-77) with some modifications. In the case of the CSE enzyme, an assay consist of a 100 µL reaction mixture containing 5 µg of the purified CSE enzyme, 0.01 mM PLP, 1 mM L-cys, and 50 mM sodium phosphate buffer pH 8.2. For the CBS enzyme, the reaction mixture contains the same as for the CSE plus 1 mM homocysteine. The inhibitors can be added to the reaction before L-cys is added to the solution. Reactions are initiated by transferring the reaction solutions from ice to a 37° C. shaking water bath. After incubation at 37° C. the reaction is terminated by adding 1% ZnAc to trap $H_2S$ followed by 10% TCA to precipitate proteins. Subsequently, N,N-dimethyl-p-phenylenediamine-sulfate in 7.2 M HCl was immediately followed by addition of $FeCl_3$ in 1.2 M HCl. The absorbance of the resulting solution is measured at 655 nm. $H_2S$ content is calculated against a calibration curve of standard $H_2S$ solutions. GST need not be removed from the fusion proteins as it has been previously reported that the presence of GST does not affect activity. Furthermore, GST does not interfere with the assay, since no $H_2S$-synthesizing activity is observed in a control activity experiment with GST alone (Huang et al., (2010) *J Mol Biol* 396:708-18).

Materials.

L-cys, D-cysteine, homocysteine, PLP, d-aminolevulinic acid (d-ALA), GSH, protease inhibitor cocktail, Coomassie blue R-250, zinc acetate (ZnAc), trichloroacetic acid (TCA), N,N-dimethyl-p-phenylenediamine-sulfate, iron(III) chloride ($FeCl_3$), phenylephrine (PE), sodium hydrogen sulfide (NaSH), DL-PAG, b-cyano-L-alanine (BCA), HA, AOAA, methyl selenocysteine, isoniazid, hydralazine, trifluoroalanine, aminoethoxyvinylglycine (AVG) and pargyline were obtained from Sigma-Aldrich (Taufkirchen, Germany). D-cycloserine was obtained from ABCR GmbH & Co KG (Karlsruhe, Germany). *Escherichia coli* BL21 (DE3) Codon Plus cells were obtained from Stratagene. Luria-Bertani (LB) broth medium and agar were purchased from Fischer Scientific (Loughborough, UK). GSTrap FF columns were obtained from GE Healthcare (Uppsala, Sweden). Isopropyl-β-Dthiogalactopyranoside (IPTG), TritonX-100, DTT, tetramethylethylenediamine, ammonium persulfate, and ampicillin were obtained from Applichem Biochemica (Darmstadt, Germany). PBS, tris/glycine/SDS buffer (TGF), Tris-HCl, PVDF membrane and DC protein assay kit were obtained from Biorad (Hercules, Calif., USA). RIPA, NuPAGE LDS sample buffer and NuPAGE sample-reducing agent were purchased from Invitrogen (Carlsbad, Calif., USA); Starting Block T20 blocking buffer and chemiluminescent substrate were purchased from Thermo Scientific (BioAnalytica S.A, Athens, Greece). CBS antibody was obtained from Abnova (Aachen, Germany) and CSE antibody was purchased from ProteinTech (Herford, Germany). Secondary antibodies were purchased from Cell Signaling Technologies (Beverly, Mass., USA).

Example 3

YD-2-51 for the Treatment of Colon Cancer

All commercially available starting materials and solvents were reagent grade and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). NMR spectra were recorded on a Bruker-300 ($^1$H, 300 MHz; $^{13}$C, 75 MHz) spectrometer. $^1$H and $^{13}$C NMR spectra were recorded with TMS as an internal reference. Chemical shifts downfield from TMS were expressed in ppm, and J values were given in Hz. High-resolution mass spectra (HRMS) were obtained from Thermo Fisher LTQ Orbitrap Elite mass spectrometer. Parameters include the following: nano ESI spray voltage was 1.8 kV, capillary temperature was 275° C., and the resolution was 60000; ionization was achieved by positive mode. Reagents and conditions: (a) $(CH_3CH_2)_2CHBr$, $K_2CO_3$, DMF, 50° C., 12 h; (b) TFA, $CH_2Cl_2$, rt, 2 h.

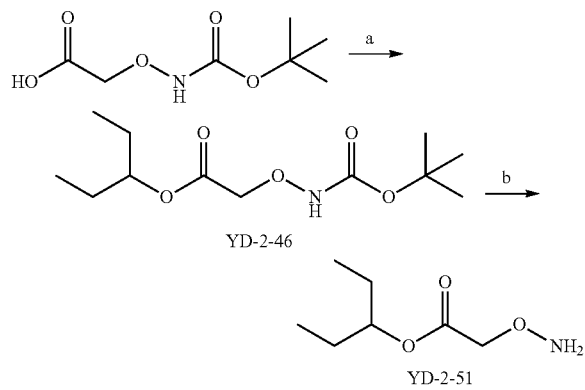

YD-2-46

YD-2-51

Synthesis of pentan-3-yl 2-(((tert-butoxycarbonyl)amino)oxy)acetate (YD-2-46)

To a mixture of (Boc-aminooxy)acetic acid (126.7 mg, 0.66 mmol) in DMF (10 mL) was added $K_2CO_3$ (366.5 mg, 2.65 mmol) and 3-bromopentane (109.7 mg, 0.72 mmol) at room temperature. The resulting mixture was stirred at 50° C. for 12 h. Then the solvent was removed under reduced pressure and the residue was dissolved in EtOAc (25 mL). The organic layer was washed with water (25 mL) and brine (25 mL), dried over anhydrous $Na_2SO_4$, filtered, and evaporated to give an oily residue. The residue was purified using silica gel column; elution with 6.6% EtOAc in hexane afforded the desired product YD-2-46 (100.5 mg, 58%) as a colorless gel. $^1$H NMR (300 MHz, $CDCl_3$) δ 7.87 (s, 1H), 4.87 (dd, J=11.9, 5.7 Hz, 1H), 4.41 (s, 2H), 1.58 (m, 4H), 1.46 (s, 9H), 0.87 (t, J=7.2 Hz, 6H). $^{13}$C NMR (75 MHz, $CDCl_3$): δ 169.55, 156.25, 81.95, 78.05, 72.47, 28.13, 28.13, 28.13, 26.34, 26.34, 9.52, 9.52.

Synthesis of pentan-3-yl 2-(aminooxy)acetate (YD2-51)

To a mixture of YD-2-46 (100.3 mg, 0.38 mmol) in $CH_2Cl_2$ (2 mL) was added TFA (0.5 mL) dropwise at 0° C. The resulting mixture was stirred at room temperature for 2 h. The mixture was diluted with $CH_2Cl_2$ (25 mL), washed by $Na_2CO_3$ aqueous solution (25 mL) and brine (25 mL), dried over anhydrous $Na_2SO_4$, and evaporated to give crude product. It was purified using silica gel column; elution with 33% EtOAc in hexane afforded the desired product YD2-51 (38.4 mg, 62%) as colorless gel. $^1$H NMR (300 MHz, $CDCl_3$): δ 5.89 (s, 2H), 4.89 (m, 1H), 4.25 (s, 2H), 1.61 (m, 4H), 0.91 (t, J=7.4 Hz, 6H). $^{13}$C NMR (75 MHz, $CDCl_3$): δ 170.66, 77.52, 72.48, 26.46, 26.46, 9.59, 9.59. HRMS Calcd for $C_7H_{16}NO_3$: $[M+H]^+$ 162.1130. found 162.1124.

Inhibition of Colon Cancer Cell Proliferation by YD2-51.

For assessment of cell proliferation, the xCELLigence system (Roche) was used. Briefly, HCT116 cells were cultured until approximately 70% confluence. Cells were then detached by Trypsin-EDTA and resuspended in fresh culture media at a concentration of 30,000 cells/ml. 200 μl of cell suspension was added to each well (6,000 cells/well) of a E-plate 96, a specially designed 96-well microtiter plate containing interdigitated microelectrodes to non-invasively monitor the cell proliferation by measuring the relative change in the electrical impedance of the cell monolayer, a unitless parameter named cell index (CI). Cells were then treated with YD02-51 and proliferation was monitored for 48 hours. YD2-51 induced a potent, concentration-dependent inhibition of tumor cell proliferation.

Inhibition of Tumor Growth by YD2051 in Tumor-Bearing Mice.

Nu/nu Balb/c female mice (8-10 weeks) were injected subcutaneously in the right and left dorsum ($10^6$ cells/side with HCT116 cells). One week later, the mice were randomized and subcutaneous injection of phosphate buffered saline (PBS control) or YD2-51 (0.1, 0.5 or 1 mg/kg) was performed 6 days/week. Tumor volumes and final weights at harvest (post-tumor injection Day 28) were performed and tumor weight/animal weight ratios calculated. YD0251 inhibited tumor growth in the mice.

The invention claimed is:

1. A cystathionine-β-synthase (CBS) inhibitor having a chemical structure of Formula I,

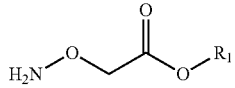

Formula I wherein $R_1$ is a 3-pentyl group, wherein the compound inhibits CBS.

SEQUENCE LISTING

<160> NUMBER OF SEQ ID NOS: 2

<210> SEQ ID NO 1
<211> LENGTH: 58
<212> TYPE: DNA
<213> ORGANISM: Artificial Sequence

```
<220> FEATURE:
<223> OTHER INFORMATION: Synthetic oligonucleotide

<400> SEQUENCE: 1
ccggcttgcc agatattctg aagaactcga gttcttcaga atatctggca agtttttg        58

<210> SEQ ID NO 2
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 2
ccgggcggaa ctacatgacc aagttctcga gaacttggtc atgtagttcc gctttttg        58
```